US010125355B2

(12) United States Patent
Yokoyama et al.

(10) Patent No.: US 10,125,355 B2
(45) Date of Patent: Nov. 13, 2018

(54) PROTEIN HAVING B-GLUCOSIDASE ACTIVITY AND USES THEREOF

(71) Applicant: MEIJI SEIKA PHARMA CO., LTD., Chuo-ku, Tokyo (JP)

(72) Inventors: Fumikazu Yokoyama, Odawara (JP); Kengo Yokoyama, Odawara (JP); Nobuko Mazuka, Odawara (JP)

(73) Assignee: MEIJI SEIKA PHARMA CO., LTD., Tokyo (JP)

( * ) Notice: Subject to any disclaimer, the term of this patent is extended or adjusted under 35 U.S.C. 154(b) by 0 days.

(21) Appl. No.: 14/576,793

(22) Filed: Dec. 19, 2014

(65) Prior Publication Data

US 2015/0104833 A1 Apr. 16, 2015

Related U.S. Application Data

(62) Division of application No. 13/391,598, filed as application No. PCT/JP2010/063844 on Aug. 17, 2010, now Pat. No. 8,975,057.

(30) Foreign Application Priority Data

Aug. 20, 2009 (JP) ................................ 2009-190840

(51) Int. Cl.
| | |
|---|---|
| *C12N 9/42* | (2006.01) |
| *C12P 19/14* | (2006.01) |
| *D21C 5/00* | (2006.01) |
| *D21H 17/00* | (2006.01) |
| *D06M 15/15* | (2006.01) |
| *A23K 10/32* | (2016.01) |
| *A23K 10/14* | (2016.01) |
| *D21H 17/22* | (2006.01) |
| *D21H 21/10* | (2006.01) |

(52) U.S. Cl.
CPC ............ *C12N 9/2445* (2013.01); *A23K 10/14* (2016.05); *A23K 10/32* (2016.05); *C12P 19/14* (2013.01); *C12Y 302/01021* (2013.01); *D06M 15/15* (2013.01); *D21C 5/005* (2013.01); *D21H 17/005* (2013.01); *D21H 17/22* (2013.01); *D21H 21/10* (2013.01)

(58) Field of Classification Search
CPC .................................................. C12N 9/2445
See application file for complete search history.

(56) References Cited

U.S. PATENT DOCUMENTS

| | | | |
|---|---|---|---|
| 2004/0091469 A1 | 5/2004 | Fukasawa | |
| 2008/0201805 A1* | 8/2008 | Krogh | .................. C12N 9/2477 800/298 |

FOREIGN PATENT DOCUMENTS

| | | |
|---|---|---|
| EP | 0927756 | 7/1999 |
| JP | 60043954 | 3/1985 |
| JP | 04117244 | 4/1992 |
| JP | 07236431 | 9/1995 |
| JP | 07264994 | 10/1995 |
| JP | 10066569 | 3/1998 |
| JP | 2000069978 | 3/2000 |
| JP | 2001017180 | 1/2001 |
| JP | 2002101876 | 4/2002 |
| WO | 9733982 | 9/1997 |
| WO | 9911767 | 3/1999 |
| WO | 0226979 | 4/2002 |

OTHER PUBLICATIONS

GenBank accessioon No. KUL82503.1 (Jan. 2016).*
Surfactants: The Ubiquitous Amphiphiles, retrieved from http://www.rsc.org/chemistryworld/issues/2003/july/amphiphiles.asp on Mar. 13, 2014.*
H. Guo et al., "Protein Tolerance to Random Amino Acid Change", PNAS 101(25): 9205-9210. (Year: 2004).*
Yamanobe et al., "Isolation of a Cellulolytic Enzyme Producing Microorganism, Culture Conditions and Some Properties of the Enzymes," Agric. Biol. Chem., 51(1):65-74 (1987).
Fedorova et al., Accession No. B6QHN4, Database DDBJ/EMBL/GenBank [online], <http://www.uniprot.org/uniprot/B6QHN4> Definition: Beta-D-glucoside glucohydrolase uploaded Dec. 16, 2008.
Fedorova et al., Accession No. DS995902, Database DDBJ/EMBL/GenBank [online], http://www.ncbi.nim.nih.gov/sviewer/viewer.fcgi?val=210068314&sat=WGS2&satkey=37592451 Definition: Penicillium marneffei ATCC 18224 scf_1105668340752 genomic scaffold, whole genome shotgun sequence, uploaded Oct. 29, 2008.
Fedorova et al., Accession No. B8MJH5, Database DDBJ/EMBL/GenBank [online], <http://www.uniprot.org/uniprot/B8MJH5> Definition: Beta-D-glucoside glucohydrolase uploaded Mar. 3, 2009.
Fedorova et al., Accession No. EQ962657, Database DDBJ/EMBL/GenBank [online], <http://www.ncbi.nlm.nih.gov/nuccore/218715133>, Definition: Talaromyces stipitatus ATCC 10500 scf_1105507295515 genomic scaffold, whole genome shotgun sequence, uploaded Dec. 22, 2008.
English Translation of International Preliminary Report on Patentability issued in PCT/JP2010/063844 dated Mar. 22, 2012.
Fang et al., "Strain improvement of Acremonium cellulolyticus for cellulase production by mutation", J. of Bioscience and Bioengineering, 107(3):256-261 (2009).

(Continued)

*Primary Examiner* — Rebecca E Prouty
(74) *Attorney, Agent, or Firm* — Sughrue Mion, PLLC

(57) ABSTRACT

By combination of hydrophobic chromatography and strongly basic anion-exchange chromatography, a novel, highly hydrophobic β-glucosidase was successfully identified from *Acremonium cellulolyticus*. Further, a gene corresponding to the identified β-glucosidase was isolated. When multiple modifications were introduced into the base sequence of the gene, the gene was successfully expressed in *Trichoderma viride* at a high level, and the expression product successfully exhibited a high β-glucosidase activity.

9 Claims, 1 Drawing Sheet
Specification includes a Sequence Listing.

(56) References Cited

OTHER PUBLICATIONS

Communication for EP 10809957 dated Feb. 7, 2013, with Supplementary European Search Report.
Kansarn et al., "Purification and Characterization of three (β-glucosidases from Acremonium cellulolyticus", Shizuoka Daigaku Daigakuin Denshi Kagaku Kenkyuu-ka Kenkyuu Houkoku, 21:9-15 (2000).
UniProt Accession No. B6QHN4 (Dec. 2008).

* cited by examiner

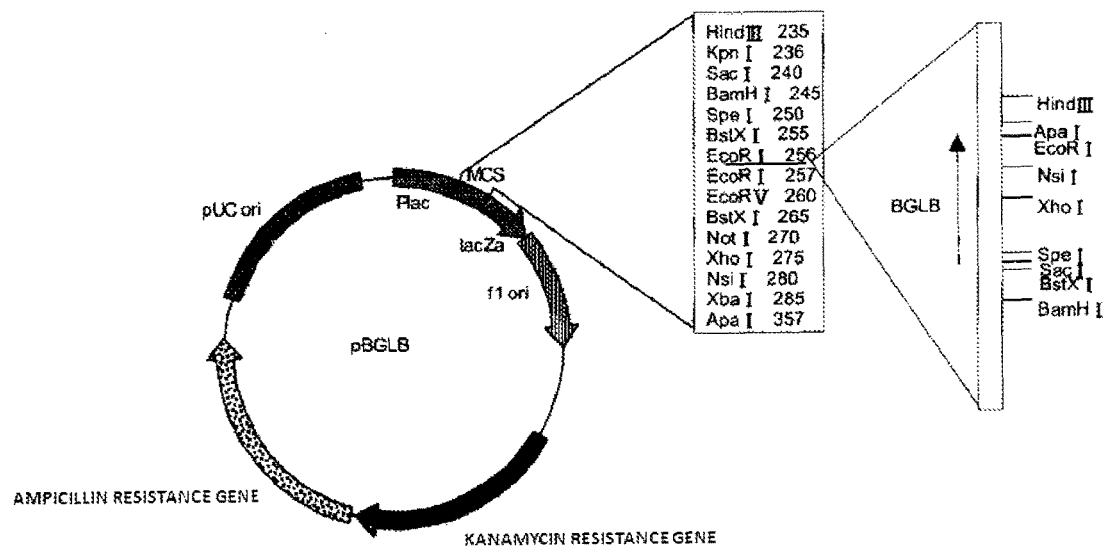

PROTEIN HAVING β-GLUCOSIDASE ACTIVITY AND USES THEREOF

CROSS REFERENCE TO RELATED APPLICATIONS

This application is a Divisional of U.S. application Ser. No. 13/391,598, filed Feb. 21, 2012 (now allowed); which is a National Stage of International Application No. PCT/JP2010/063844 filed Aug. 17, 2010; which claims priority based on Japanese Patent Application No. 2009-190840 filed Aug. 20, 2009; the contents of all of which are incorporated herein by reference in their entirety.

TECHNICAL FIELD

The present invention relates to a novel protein having a β-glucosidase activity and uses thereof. Specifically, the present invention relates to a novel protein having a β-glucosidase activity derived from *Acremonium cellulolyticus*, an analog and a variant of the protein, polynucleotides encoding these proteins, and a production method for and uses of these proteins.

BACKGROUND ART

Cellulose is an essential constitutive component of cells of higher plants, and widely exists in nature. Cellulose is a polysaccharide polymer of glucose units polymerized through a β-1,4-glycosidic bond. In nature, cellulose exists in a crystalline or amorphous state. By bonding to other components such as lignin, hemicelluloses, and pectins in a complicated manner, cellulose constructs plant tissues.

Cellulase is a generic term of a group of enzymes that breaks down cellulose. Generally, cellulase produced by microorganisms includes various types of cellulase components. In accordance with the substrate specificity, the cellulase components are classified into three types: cellobiohydrolase, endoglucanase, and β-glucosidase. *Aspergillus niger* that is a cellulase-producing filamentous fungus is believed to produce 4 types of cellobiohydrolases at maximum, 15 types of endoglucanases, and 15 types of β-glucosidases. Presumably, multiple enzymes among these acting in various reaction modes compensate for each other to exhibit synergistic effects, thereby breaking down cellulose which is an essential component of plant cell walls. It is believed that β-glucosidase catalyzes a reaction to release glucose from cello-oligosaccharides, cellobiose or glycosides with aglycone linked thereto through β-D-glucopyranosyl linkage. β-glucosidase is an important enzyme in the final stage of cellulose saccharification and in releasing glucose from glycoside.

Ethanol conversion from biomass has advantages that: the raw material is more readily available, combustion of the raw material or burying in the ground can be avoided, and ethanol fuel is environmentally clean. Woods, agricultural residues, herbaceous crops and municipal solid wastes have drawn attention as biomass for ethanol production. These materials are mainly composed of cellulose, hemicellulose and lignin. Once cellulose is converted into glucose, the glucose is easily fermented into ethanol by yeasts. On the other hand, cellobiose is not easily fermented into ethanol by yeasts, and accordingly the remaining cellobiose causes ethanol yield reduction. What is more important is that cellobiose is a potent inhibitor of endoglucanases and cellobiohydrolases. For this reason, the accumulation of cellobiose during hydrolysis is not desirable for production of ethanol. Generally, cellulase-producing microorganisms can hardly produce β-glucosidases. This brings about a major problem that cellobiose produced by enzymatic hydrolysis is accumulated.

In order to promote conversion from cellobiose to glucoses, the yield of β-glucosidases is increased by over-expression of β-glucosidases in a host. Thus, it is effective means for promoting saccharification from biomass to glucose. Accordingly, isolation of a novel β-glucosidase gene which is introduced and expressed in cellulase-producing microorganisms has been desired.

Meanwhile, filamentous fungus *Acremonium cellulolyticus* has been reported to produce a cellulase having a strong saccharification power (Non Patent Literature 1) and to be highly useful for feed and silage usages (Patent Literatures 1 to 3). In addition, the cellulase component contained therein (Patent Literatures 4 to 10) has also been examined in detail. It has been revealed that various kinds of cellulase component are secreted as in other filamentous fungi. Particularly, as to the β-glucosidase activity of the cellulase therein, it has been reported, for example, that the activity is significantly higher than those of cellulases from *Trichoderma reesei* and the like (Patent Literature 11). Because of such characteristics, attention has been focused on *Acremonium cellulolyticus* as the target from which a β-glucosidase gene is isolated.

However, only a few genes have been isolated from *Acremonium cellulolyticus* so far (Patent Literatures 9, 10). Further, the isolated genes have not yet been successfully expressed in filamentous fungi other than *Acremonium cellulolyticus*.

CITATION LIST

Patent Literatures

[PTL 1] Japanese Unexamined Patent Application Publication No. Hei 7-264994
[PTL 2] Japanese Patent No. 2531595
[PTL 3] Japanese Unexamined Patent Application Publication No. Hei 7-236431
[PTL 4] Japanese Unexamined Patent Application Publication No. 2001-17180
[PTL 5] International Publication No. WO97/33982
[PTL 6] International Publication No. WO99/011767
[PTL 7] Japanese Unexamined Patent Application Publication No. 2000/69978
[PTL 8] Japanese Unexamined Patent Application Publication No. Hei 10-066569
[PTL 9] Japanese Unexamined Patent Application Publication No. 2002/101876
[PTL 10] International Publication No. WO2002/026979
[PTL 11] Japanese Examined Patent Application Publication No. Sho 60-43954

Non Patent Literature

[NPL 1] "Agricultural and Biological Chemistry," (Japan), 1987, Vol. 51, p. 65

SUMMARY OF INVENTION

Technical Problem

The present invention has been made in view of such circumstances. An object of the present invention is to isolate a novel β-glucosidase gene from *Acremonium cel-*

*lulolyticus*. Another object of the present invention is to increase the yield of β-glucosidase from a host in which the isolated β-glucosidase gene is expressed at a high level.

Solution to Problem

To achieve the above-described objects, the present inventors have earnestly studied methods of separating and purifying a β-glucosidase derived from *Acremonium cellulolyticus*. As a result, the inventors have finally successfully identified a novel β-glucosidase different from β-glucosidases that have been known so far from *Acremonium cellulolyticus*. Moreover, a gene encoding the identified β-glucosidase has also been successfully isolated. The β-glucosidase gene found out by the present inventors had not been isolated despite attempts over the years to isolate the gene from *Acremonium cellulolyticus*. The reason is presumably that since the hydrophobicity of a protein encoded by the gene is high, this makes the separation and purification thereof difficult.

Further, the present inventors have earnestly studied methods of expressing the isolated β-glucosidase gene derived from *Acremonium cellulolyticus* at a high level in a host, thereby causing the host to produce a β-glucosidase having an excellent activity. As a result, by introducing modification of multiple bases into the β-glucosidase gene, successfully, for the first time in the world, high-level expression of a β-glucosidase gene was achieved in filamentous fungi other than *Acremonium cellulolyticus*, and the expression product exhibited a high β-glucosidase activity. This makes it possible to express a β-glucosidase derived from *Acremonium cellulolyticus* at a high level in a host, and to increase an amount of β-glucosidase produced. The present inventors have found out that by using the β-glucosidase or a cellulase preparation obtained from the transformant thus prepared, saccharification from biomass to glucose and various treatments and modifications on a cellulose-based substrate can be efficiently carried out. This discovery has led to the completion of the present invention.

Specifically, the present invention relates to a novel protein having a β-glucosidase activity derived from *Acremonium cellulolyticus*, an analog and a variant of the protein, polynucleotides encoding these proteins, and a production method for and uses of these proteins. More specifically, the present invention provides the followings.

(1) A polynucleotide of any one of the following (i) to (vi), which encodes a protein having a β-glucosidase activity:
 (i) a polynucleotide encoding a protein comprising an amino acid sequence of SEQ ID NO: 3;
 (ii) a polynucleotide comprising a coding region of a base sequence of any one of SEQ ID NOs: 1 and 2;
 (iii) a polynucleotide encoding a protein comprising an amino acid sequence of SEQ ID NO: 3 in which one or more amino acids are substituted, deleted, inserted and/or added;
 (iv) a polynucleotide encoding a protein comprising an amino acid sequence having an identity of 90% or more with the amino acid sequence of SEQ ID NO: 3;
 (v) a polynucleotide hybridizing under stringent conditions with a polynucleotide comprising the base sequence of any one of SEQ ID NOs: 1 and 2; and
 (vi) a polynucleotide of any one of (i) to (v) from which a base sequence encoding a signal sequence is removed.
(2) The polynucleotide according to (1), which is derived from a filamentous fungus.
(3) The polynucleotide according to (2), wherein the filamentous fungus is *Acremonium cellulolyticus*.
(4) A polynucleotide of any one of the following (i) and (ii), which encodes a protein having a β-glucosidase activity:
 (i) a polynucleotide encoding a protein comprising an amino acid sequence of SEQ ID NO: 3; and
 (ii) a polynucleotide comprising a coding region of a base sequence of SEQ ID NO: 4.
(5) A polynucleotide comprising a base sequence of SEQ ID NO: 4 in which one or more bases are substituted, deleted, inserted and/or added, the polynucleotide encoding a protein having a β-glucosidase activity and being expressible in *Trichoderma viride*.
(6) The polynucleotide according to (5), being capable of improving a β-glucosidase activity when expressed in a *Trichoderma viride* transformant 5 times or more in comparison with a β-glucosidase activity in *Trichoderma viride* parental strain.
(7) The polynucleotide according to any one of (4) to (6), from which a base sequence encoding a signal sequence is removed.
(8) An expression vector comprising the polynucleotide according to any one of (1) to (7).
(9) A host cell transformed with the expression vector according to (8).
(10) A protein encoded by the polynucleotide according to any one of (1) to (7).
(11) The protein according to (10), which is a recombinant protein.
(12) A method for producing the protein according to (11), the method comprising the steps of:
 culturing the host cell according to (9); and
 harvesting a protein expressed from the host cell and/or a culture thereof.
(13) A cellulase preparation comprising the protein according to (11).
(14) A method for degrading or converting a cellulose material, the method comprising the steps of:
 treating the cellulose material with any one of the protein according to (10) and the cellulase preparation according to (13).
(15) A method for producing a degraded or converted cellulose material, the method comprising the steps of:
 treating a cellulose material with any one of the protein according to (10) and the cellulase preparation according to (13); and
 collecting a degraded cellulose material.
(16) The method according to (15), wherein the degraded cellulose material is a sugar.
(17) A detergent composition comprising any one of the protein according to (10) and the cellulase preparation according to (13).
(18) A method for treating a cellulose-containing fiber, the method comprising the steps of:
 bringing into contact any one of the protein according to (10), the cellulase preparation according to (13), and detergent composition the according to (17) with the cellulose-containing fiber.
(19) A method for deinking waste paper, the method characterized in that any one of the protein according to (10) and the cellulase preparation according to (13) is used in a deinking step of treating the waste paper with a deinking agent.
(20) A method for producing paper pulp having an improved drainage, the method comprising the steps of:
 treating paper pulp with any one of the protein according to (10) and the cellulase preparation according to (13).
(21) A method for producing an animal feed having an improved digestibility, the method comprising the step of:

treating an animal feed with any one of the protein according to (10) and the cellulase preparation according to (13).

(22) A filamentous fungus expressing a reduced amount of a protein encoded by the polynucleotide according to (2).

Advantageous Effects of Invention

The present invention provides a novel β-glucosidase gene derived from *Acremonium cellulolyticus*, and an analog and a variant of the gene for efficiently expressing a β-glucosidase in a host. Further, the present invention provides a host which expresses the β-glucosidase at a high level, and which shows an excellent β-glucosidase activity. This makes it possible to obtain a β-glucosidase derived from *Acremonium cellulolyticus* as a purified protein or a cellulase preparation in high yield.

BRIEF DESCRIPTION OF DRAWING

FIG. 1 is a scheme showing a restriction enzyme map of a plasmid pBGLB.

DESCRIPTION OF EMBODIMENTS

Protein Having β-Glucosidase Activity and Polynucleotide Encoding the Protein

The present invention provides a novel protein having a β-glucosidase activity and a polynucleotide encoding the protein. In the present invention, the "β-glucosidase" means an enzyme showing a β-glucosidase activity, that is, β-D-Glucoside glucohydrolase EC3.2.1.21. The "β-glucosidase activity" means an activity of hydrolyzing cello-oligosaccharides, cellobiose, or glycosides with aglycone linked thereto through β-D-glucopyranosyl linkage by an exo-mechanism to produce glucose.

The "polynucleotide" encoding the protein having a β-glucosidase activity of the present invention includes, for example, a DNA, a RNA, modified products or chimeras thereof, and is preferably a DNA. The DNA includes a cDNA, a genomic DNA, and a chemically synthesized DNA. The base sequence of a cDNA which is isolated by the present inventors, and which encodes the novel β-glucosidase (hereinafter, referred to as "acBGLB") derived from *Acremonium cellulolyticus*, is shown in SEQ ID NO: 1. The base sequence of the genomic DNA is shown in SEQ ID NO: 2. Moreover, the amino acid sequence of the acBGLB encoded by these DNAs is shown in SEQ ID NO: 3.

A preferable embodiment of the polynucleotide of the present invention is a polynucleotide encoding the acBGLB comprising the amino acid sequence of SEQ ID NO: 3. An example thereof includes a polynucleotide comprising a coding region of the base sequence of any one of SEQ ID NOs: 1 and 2.

Moreover, the present invention comprises a polynucleotide encoding a protein functionally equivalent to the acBGLB. Examples of such a polynucleotide include mutants, derivatives, alleles, variants and homologs of the acBGLB. Herein, the phrase "functionally equivalent" means that the target protein has a β-glucosidase activity. Preferably, when compared, the target protein has 70% or more, preferably 80% or more, more preferably 90% or more, and most preferably 95% or more of the β-glucosidase activity of the acBGLB. The β-glucosidase activity of the target protein and the acBGLB can be evaluated as an activity of producing 1 μmol of p-nitrophenol from p-nitrophenyl-β-glucoside in 1 minute when measured by a method described in the literature (Methods in ENZYMOLOGY, vol. 160, Biomass Part A Cellulose and Hemicellulose, Willis A. Wood ed. p 109-110).

One embodiment of the polynucleotide encoding a protein functionally equivalent to the acBGLB is a polynucleotide encoding a protein having a β-glucosidase activity, the protein comprising an amino acid sequence of SEQ ID NO: 3 in which one or more amino acids are substituted, deleted, and/or added.

The number of amino acid residues modified is preferably 1 to 40, more preferably 1 to 20, further preferably 1 to 8, and most preferably 1 to 4. The modification of amino acids is preferably conservative substitution. The "conservative substitution" means that at least one amino acid residue is substituted with another chemically similar amino acid residue in such a manner as not to substantially change the activity of the polypeptide. Examples thereof include a case where a certain hydrophobic amino acid residue is substituted with another hydrophobic amino acid residue, a case where a certain polar amino acid residue is substituted with another polar amino acid residue having the same charge, and other cases. Functionally similar amino acids which can be subjected to such substitution are known to those skilled in the art for each amino acid. Specific examples of non-polar (hydrophobic) amino acids include alanine, valine, isoleucine, leucine, proline, tryptophan, phenylalanine, methionine, and the like. Specific examples of polar (neutral) amino acids include glycine, serine, threonine, tyrosine, glutamine, asparagine, cysteine, and the like. Specific examples of positively-charged (basic) amino acids include arginine, histidine, lysine, and the like. Further, specific examples of negatively-charged (acidic) amino acids include aspartic acid, glutamic acid, and the like.

The polynucleotide encoding the protein having a β-glucosidase activity of the present invention is preferably a polynucleotide encoding a protein comprising an amino acid sequence of SEQ ID NO: 3 (for example, a polynucleotide comprising a coding region of a base sequence of SEQ ID NO: 4), particularly when expressed in *Trichoderma viride*. In the base sequence of SEQ ID NO: 4, 13.2% or more of the bases are modified in comparison with the base sequence (SEQ ID NO: 1) of the polynucleotide encoding the acBGLB. In determining a codon corresponding to each amino acid, the frequency distribution of codons used in a host is taken into consideration. This enables the expression in *Trichoderma viride*, and the expression product successfully exhibits a high β-glucosidase activity. Once such a preferable sequence is obtained, those skilled in the art could, on the basis of this sequence, further modify the base sequence to obtain a polynucleotide expressible in *Trichoderma* in the same manner as the polynucleotide comprising the coding region of the base sequence of SEQ ID NO: 4. Thus, the present invention provides a polynucleotide comprising the base sequence of SEQ ID NO: 4 in which one or more bases (preferably 30 bases or less, more preferably 20 bases or less, further preferably 10 bases or less, and still further preferably 5 bases or less) are substituted, deleted, inserted and/or added, the polynucleotide encoding a protein having a β-glucosidase activity and being expressible in *Trichoderma viride*. A preferable embodiment of such a polynucleotide is a polynucleotide capable of improving a β-glucosidase activity when expressed in a *Trichoderma viride* transformant 5 times or more (preferably, 7 times or more) in comparison with a β-glucosidase activity in a *Trichoderma viride* parental strain (original *Trichoderma viride* strain not deficient in a gene for uracil biosynthesis) (see Example 5).

In the present invention, another embodiment of the polynucleotide encoding a protein functionally equivalent to the acBGLB is a polynucleotide encoding a protein having a β-glucosidase activity, the protein comprising an amino acid sequence having an identity of 90% or more with the amino acid sequence of SEQ ID NO: 3. Herein, the "identity" is a numerical value calculated by using the default (initial setting) parameters in FASTA3 [Science, 227, 1435-1441(1985), Proc. Natl. Acad. Sci. USA, 85, 2444-2448 (1988), http://www.ddbj.nig.ac.jp/E-mail/homology-j.html] that is a homology search program known to those skilled in the art. The identity can be preferably an identity of 95% or more, further preferably an identity of 98% or more, and particularly preferably an identity of 99% or more.

In the present invention, another embodiment of the polynucleotide encoding a protein functionally equivalent to the acBGLB is a polynucleotide encoding a protein having a β-glucosidase activity, the polynucleotide hybridizing under stringent conditions with a polynucleotide comprising the base sequence of any one of SEQ ID NOs: 1 and 2. Herein, the "stringent conditions" mean that under which a membrane washing procedure after the hybridization is carried out at high temperature in a solution having a low salt concentration, and means washing conditions, for example, at 2×SSC concentration (1×SSC: 15 mmol/L of trisodium citrate and 150 mmol/L of sodium chloride) and in a 0.5% SDS solution at 60° C. for 20 minutes.

Further, the present invention provides a polynucleotide encoding the acBGLB or a protein functionally equivalent thereto, from which a base sequence encoding a signal sequence is removed. The signal sequence of the acBGLB is an amino acid sequence from positions −18 to −1 in the amino acid sequence of SEQ ID NO: 3.

Any polypeptide sequence may be added to the N-terminus and/or the C-terminus of each amino acid sequence corresponding to a mature protein portion of the protein of the present invention in such a manner as not to influence the β-glucosidase activity. Examples of such a polypeptide sequence include a signal sequence, a detection marker (for example, a FLAG tag), and a purification polypeptide [for example, glutathione S-transferase (GST)].

The polynucleotide encoding the protein having a β-glucosidase activity of the present invention can be prepared by utilizing conventional means for those skilled in the art. In preparing a genomic DNA encoding the protein having a β-glucosidase activity of the present invention, for example, first, a genomic DNA is extracted from a target microorganism such as Acremonium cellulolyticus by a generally-used method. The genomic DNA is digested with an appropriate restriction enzyme and then ligated to an appropriate vector. Thereby, a genomic DNA library of Acremonium cellulolyticus is prepared. As the vector, various vectors can be used such as, for example, a plasmid vector, a phage vector, a cosmid vector, and a BAC vector. Next, an appropriate probe is prepared based on the base sequence (for example, SEQ ID NO: 2) of the polynucleotide encoding the protein having a β-glucosidase activity of the present invention, and a desired genomic DNA can be isolated from the genomic DNA library through hybridization. Alternatively, a primer is prepared based on the base sequence (for example, SEQ ID NO: 2) of the polynucleotide encoding the protein having a β-glucosidase activity of the present invention, and PCR is performed using the genomic DNA of Acremonium cellulolyticus as a template. A DNA fragment thus amplified is ligated to an appropriate vector. Accordingly, a desired genomic DNA can be isolated. Meanwhile, in preparing a cDNA encoding the protein having a β-glucosidase activity of the present invention, for example, first, a cDNA is synthesized based on an mRNA extracted from a target microorganism such as Acremonium cellulolyticus. The cDNA is digested with an appropriate restriction enzyme and then ligated to an appropriate vector. Thereby, a cDNA library of Acremonium cellulolyticus is prepared. Next, an appropriate probe is prepared based on the base sequence (for example, SEQ ID NO: 1) of the polynucleotide encoding the protein having a β-glucosidase activity of the present invention, and a desired cDNA can be isolated from the cDNA library through hybridization. Alternatively, a primer is prepared based on the base sequence (for example, SEQ ID NO: 1) of the polynucleotide encoding the protein having a β-glucosidase activity of the present invention, and PCR is performed using the cDNA of Acremonium cellulolyticus as a template. A DNA fragment thus amplified is ligated to an appropriate vector. Accordingly, a desired cDNA can be isolated. Furthermore, the polynucleotide encoding the protein having a β-glucosidase activity of the present invention can be obtained artificially by chemical synthesis.

The present invention provides an expression vector comprising: the polynucleotide encoding the protein having a β-glucosidase activity of the present invention, the polynucleotide being replicable in a host microorganism; and the protein encoded from the polynucleotide sequence in an expressible state. The expression vector of the present invention can be constructed based on a self-replicating vector, i.e., for example, a plasmid which exists as an extrachromosomal element, and which replicates independently of the replication of the chromosome. Alternatively, the expression vector of the present invention may be replicated together with the chromosome of the host microorganism, after introduced into the host microorganism and incorporated into the genome thereof. As a procedure and a method for constructing the expression vector of the present invention, any procedure and any method commonly used in the field of genetic engineering can be used.

To express the protein having a β-glucosidase activity after the expression vector according to the present invention is actually introduced in a host microorganism, the expression vector according to the present invention desirably comprises, in addition to the polynucleotide encoding the protein having a β-glucosidase activity of the present invention, a polynucleotide sequence for regulating the expression, a genetic marker for selecting a microorganism, and the like. Examples of the polynucleotide sequence for regulating the expression include polynucleotide sequences encoding a promoter, terminator, and signal peptide. The promoter is not particularly limited, as long as the transcriptional activity is exhibited in the host microorganism. The promoter may be derived from a microorganism either homologous or heterologous to the host microorganism. Moreover, the signal peptide is not particularly limited, as long as the signal peptide contributes to secretion of the protein in the host microorganism. The signal peptide may be derived from a microorganism either homologous or heterologous to the host microorganism. Further, the genetic marker can be selected as appropriate according to the method of selecting the transformant. For example, a gene encoding drug resistance or a gene complementing the auxotrophy can be used.

Further, the present invention provides a microorganism transformed with the expression vector. The host microorganism used in the present invention is not particularly limited. Examples thereof include filamentous fungi, yeasts, Escherichia coli, actinomycetes, and the like. Examples of the yeast cells include those belonging to the genera Sac-

*charomyces, Hansenula*, and *Pichia*. A preferable example of the yeast cell is *Saccharomyces cerevisiae*. Moreover, examples of the filamentous fungi include those belonging to the genera *Humicola, Aspergillus, Trichoderma, Fusarium,* and *Acremonium*. Preferably examples of the filamentous fungi include *Humicola insolens, Aspergillus niger, Aspergillus oryzae, Trichoderma viride, Fusarium oxysporum,* and *Acremonium cellulolyticus*. The transformation of these microorganisms with the expression vector of the present invention can be carried out according to any method commonly used in this field.

The protein having a β-glucosidase activity of the present invention (or a cellulase preparation of the present invention to be described later) can be collected from a culture (for example, cultured cell, culture supernatant) obtained by culturing the thus-prepared transformant in an appropriate medium. The culturing of the transformant and conditions therefor may be substantially the same as those for a microorganism to be used. Moreover, as the method of collecting the target protein after the transformant is cultured, any method commonly used in this field can be used. For example, after the culturing of the transformant is finished, a supernatant fluid obtained by removal from the culture by centrifugation or the like can be used as a crude enzyme. Further, this supernatant fluid is concentrated by an ultrafiltration method or the like, and an antiseptic and the like are added thereto. The resultant can be used as a concentrated enzyme. Furthermore, after the concentrating, a powdery enzyme can be prepared by a spray-dry method or the like. The protein having a β-glucosidase activity of the present invention (or the cellulase preparation of the present invention) can be obtained, as necessary, by partially purifying or highly purifying the concentrated enzyme or the powdery enzyme. As the purification method, conventional methods, for example, a salting-out method with ammonium sulfate or the like, an organic solvent precipitation method with alcohol or the like, a membrane separation method, and a chromatographic separation method using an ion exchanger, a hydrophobic chromatography carrier, a gel filtration carrier, or the like, can be used alone or in combination as appropriate. The present invention provides such a method for producing the protein having a β-glucosidase activity of the present invention (or the cellulase preparation of the present invention).

Cellulase Preparation

The present invention provides a cellulase preparation comprising the above-described protein having a β-glucosidase activity of the present invention. The cellulase preparation of the present invention may comprise a different protein from the protein having a β-glucosidase activity of the present invention. As the different protein, the cellulase preparation of the present invention may comprise, for example, a β-glucosidase other than the protein having a β-glucosidase activity of the present invention, hemicellulase, endoglucanase, cellobiohydrolase, aminopeptidase, amylase, carbohydrase, carboxypeptidase, catalase, chitinase, cutinase, cyclodextrin glycosyltransferase, deoxyribonuclease, esterase, α-galactosidase, β-galactosidase, glucoamylase, α-glucosidase, haloperoxidase, invertase, laccase, lipase, mannosidase, oxidase, pectinase, peptide glutaminase, peroxidase, phytase, polyphenol oxidase, protease, ribonuclease, transglutaminase, orxylanase. The protein different from the protein having a β-glucosidase activity of the present invention comprised in the cellulase preparation of the present invention may be derived from the transformant which expresses the protein having a β-glucosidase activity of the present invention or may be one independently added.

The cellulase preparation of the present invention may be produced while being mixed with generally-contained carrier or medium, for example, an excipient (for example, lactose, sodium chloride, sorbitol, or the like), a surfactant, an antiseptic, or the like. Moreover, the cellulase preparation of the present invention can be produced in an appropriate form, for example, powder or liquid.

Uses of Protein Having β-Glucosidase Activity or Cellulase Preparation

The present invention provides a method for degrading or converting a cellulose material, the method comprising: treating the cellulose material with any one of the protein having a β-glucosidase activity of the present invention and the cellulase preparation of the present invention. Moreover, the present invention provides a method for producing a degraded or converted cellulose material, the method comprising: treating a cellulose material; and then collecting a degraded cellulose material. The cellulose material is typically a biomass. Examples thereof include, but are not limited to, rice straw, bagasse, corn stover, pomaces of fruits such as coconut, waste wood, and materials obtained by subjecting these to an appropriate pre-treatment. The protein having a β-glucosidase activity or the cellulase preparation used for treating the cellulose material may be in the form of a crude fermentation broth from which cells are removed or not removed, or may be in the form of semi-purified or purified preparation. In the fermentation process using the biomass, the transformant of the present invention can be used as a source of producing the protein having a β-glucosidase activity of the present invention. To the transformant, various cellulase genes or a gene encoding another enzyme effective in processing the biomass may be introduced. The methods of the present invention can be utilized to produce a sugar (for example, monosaccharides, disaccharides, polysaccharides) as chemical or fermentation feedstocks from the biomass, for example. The sugar thus obtained serves as a raw material for producing, for example, ethanol, plastics, other products or intermediates.

Further, the present invention provides a detergent composition comprising any one of the protein having a β-glucosidase activity of the present invention and the cellulase preparation of the present invention. The detergent composition of the present invention may also comprise a surfactant (anionic, nonionic, cationic, amphoteric or zwitterionic surfactant, or may be a mixture of these). Moreover, the detergent composition may also comprise other detergent components known in this field, for example, a builder, a bleach, a bleach activator, a corrosion inhibitor, a sequestering agent, a soil release polymer, a flavor, other enzymes (protease, lipase, amylase, and the like), an enzyme stabilizer, a formulation aid, an optical brighter, and/or a foaming agent, and the like.

Furthermore, the present invention provides a method for treating a cellulose-containing fiber, the method comprising the steps of bringing any one of the protein having a β-glucosidase activity of the present invention, the cellulase preparation of the present invention, and the detergent composition into contact with the cellulose-containing fiber. Examples of characteristics of the cellulose-containing fiber to be improved by the treatment method of the present invention include: (1) touch feel and appearance of the fiber improved by the reduced weight, (2) local variations in color provided to the colored cellulose-containing fiber, that is, stonewashed appearance and texture provided to the colored cellulose-containing fiber, typically jeans, (3) clearness of the color of the colored cellulose-containing fiber, (4) softness (slowed timing when the material starts to stiffen, reduction in stiffness), and (5) removal of fuzz (slowed timing when fuzz starts to form, reduction in fuzz).

Furthermore, the present invention provides a method for deinking waste paper, the method characterized in that any one of the protein having a β-glucosidase activity of the present invention and the cellulase preparation of the present invention is used in a deinking step of treating the waste paper with a deinking agent.

Furthermore, the present invention provides a method for producing paper pulp having an improved drainage, the method comprising the step of: treating paper pulp with any one of the protein having a β-glucosidase activity of the present invention and the cellulase preparation of the present invention. According to the present invention, the drainage of the paper pulp can be improved without a significant reduction in strength. Examples of the paper pulp that is the treatment target include, but are not limited to, waste paper pulp, recycled paperboard pulp, Kraft pulp, sulfite pulp, thermo-mechanically treated and other high yield pulps.

Furthermore, the present invention provides a method for producing an animal feed having an improved digestibility, the method comprising the step of: treating an animal feed with any one of the protein having a β-glucosidase activity of the present invention and the cellulase preparation of the present invention. According to the method of the present invention, the digestibility of glucan in the feed in an animal body can be improved, for example.

Filamentous Fungus Expressing Reduced Amount of Protein Having β-Glucosidase Activity The present invention provides a filamentous fungus expressing a reduced amount of the protein having a β-glucosidase activity of the present invention. The filamentous fungus is preferably a filamentous fungus belonging to the genus *Acremonium*, and most preferably *Acremonium cellulolyticus*. The expression of the protein having a β-glucosidase activity of the present invention (endogenous protein) in the filamentous fungus can be reduced by utilizing general techniques such as, for example, RNA interference method, antisense RNA•DNA method, and homologous recombination. Methods of preparing polynucleotide molecules (for example, a siRNA, an antisense RNA, an antisense DNA, a polynucleotide comprising a sequence homologous to a target DNA for the recombination, and the like) used in these techniques, preparing vectors comprising these polynucleotides, and introducing the vectors into hosts are known to those skilled in the art. When cellulose widely distributed among plants and so forth is degraded by using the filamentous fungus thus produced, glucose which is a final degradation product in the degradation process is not produced, but cellobiose in which two glucose molecules are linked by a β-1,4 bond is selectively produced. Cellobiose has a sweet taste but is not degraded in human bodies. Accordingly, cellobiose is useful as a sweetener in health food and food for diabetic patients, a cosmetic raw material, or a drug raw material. By utilizing the filamentous fungus of the present invention, the raw materials of these products can be provided at reduced cost.

EXAMPLES

The present invention will be more specifically described by way of Examples. However, the present invention is not to be limited to Examples below but is still within the gist of the present invention.

Example 1

Purification of β-Glucosidase of *Acremonium cellulolyticus*

A spray-dried powdery enzyme of cellulase was prepared from *Acremonium cellulolyticus*, and dissolved in a Tris-HCl buffer (0.05 M, pH 7.0) containing 0.5 M $(NH_4)_2SO_4$. Impurities were removed therefrom by high-performance cooling centrifugation. A supernatant thus obtained was purified as a starting material for the enzyme purification according to a method shown below.

(a) Hydrophobic Chromatography (Part 1)

In a Tris-HCl buffer (0.05 M, pH 7.0) containing 0.5 M $(NH_4)_2SO_4$, a protein contained in the supernatant was adsorbed to HiTrap Butyl FF (manufactured by GE Healthcare). Then, in a Tris-HCl buffer (0.05 M, pH 7.0) containing 0.5 M to 0 M of $(NH_4)_2SO_4$, the adsorbed protein was subjected to linear gradient elution to fractionate a fraction indicating a β-glucosidase activity.

(b) Hydrophobic Chromatography (Part 2)

A protein in the fraction obtained in (a) above was again adsorbed to HiTrap Butyl FF (manufactured by GE Healthcare). Then, the adsorbed protein was subjected to linear gradient elution by the same method as in (a) to fractionate a fraction indicating a β-glucosidase activity.

(c) Strongly Basic Anion-Exchange Chromatography

In a Tris-HCl buffer (0.05 M, pH 7.0), a protein in the fraction obtained in (b) above was adsorbed to MonoQ (manufactured by GE Healthcare). The adsorbed protein was subjected to linear gradient elution in a Tris-HCl buffer (0.05 M, pH 7.0) containing 0 M to 1 M of NaCl to fractionate a fraction indicating a β-glucosidase activity.

Example 2

Determining Partial Amino Acid Sequences of Purified β-Glucosidase

The fraction having a β-glucosidase activity fractionated by the strongly basic anion-exchange chromatography in Example 1 was separated by electrophoresis using 12% Gel SDS-PAGE mini (manufactured by TEFCO), and β-glucosidase B (acBGLB) of *Acremonium cellulolyticus* was identified. A band of the acBGLB was cut out, and then reductively carboxymethylated, followed by treatment with lysyl endopeptidase. This degraded product was separated by electrophoresis using 12% Gel SDS-PAGE mini (manufactured by TEFCO), and blotted on a PVDF membrane (manufactured by Millipore Corporation). A band of the peptide fragment thus obtained was cut out. The N-terminal amino acid sequence of the peptide fragment was determined using a protein sequencer Model 492 (manufactured by Applied Biosystems Inc.). Partial amino acid sequences ("BGLB-LE-1" and "BGLB-LE-2") of the acBGLB thus determined were shown in SEQ ID NOs: 6 and 7, respectively.

Example 3

Cloning of acBGLB Gene (1) Isolation of Genomic DNA

An *Acremonium cellulolyticus* ACCP-5-1 strain was cultured in an (s) medium (2% broth, 0.5% yeast extract and 2% glucose) at 32° C. for 2 days, and the fungal cells were collected by centrifugation. A genomic DNA thereof was isolated from the obtained fungal cells according to the method by Horiuchi et al. (H. Horiuchi et. al., J. Bacteriol., 170, 272-278, (1988)).

(2) Acquisition of acBGLB Gene Fragment

Based on the partial amino acid sequences of the acBGLB, the following primers were prepared.

```
BGLB-F:
                                    (SEQ ID NO: 8)
CCNTTYGTNGGNAAYACNGCNGCNCC

BGLB-R:
                                    (SEQ ID NO: 9)
CATDATRTANCCNGGRAANCC
```

Using BGLB-F and BGLB-R as the primers and the genomic DNA as a template, PCR was performed. The PCR was performed using LA taq polymerase (manufactured by Takara Bio Inc.). The PCR was performed in 35 cycles each of "94° C. for 30 seconds, 53° C. for 30 seconds, and 72° C. for 2 minutes." The DNA fragment of 650 bp thus amplified was inserted into a pCR2.1-TOPO plasmid vector using TOPO TA cloning kit (manufactured by Invitrogen Corporation) in accordance with the protocol attached thereto. Thereby, a plasmid "TOPO-pBGLB-partial" was obtained.

The sequence of the inserted DNA fragment cloned in the plasmid "TOPO-pBGLB-partial" was determined using BigDye Terminator v3.1 Cycle Sequencing Kit (manufactured by Applied Biosystems Inc.) and ABI PRISM Genetic Analyzer (manufactured by Applied Biosystems Inc.) in accordance with the protocols attached thereto. The base sequence thus obtained was translated into the amino acid sequence. Homology search was conducted on the amino acid sequence. As a result, the amino acid sequence showed a homology of 72% with the β-glucosidase (XP_001216552) derived from *Aspergillus terreus* and a homology of 88% with the β-glucosidase (XP_002149046.1) derived from *Penicillium marneffei*. Thus, the DNA fragment was determined to be a part of the β-glucosidase (Glycoside Hydrolase family 3) gene.

(3) Acquisition of Full-Length acBGLB Gene by Inverse PCR Method

The inverse PCR method was performed according to the method by Triglia et al. (T. Triglia et. al., Nucleic Acids Research, 16, 8186, (1988)). The *Acremonium cellulolyticus* genomic DNA was digested with ScaI overnight, and a circular DNA was prepared from the digested fragment using Mighty Mix (manufactured by Takara Bio Inc.). PCR was performed using the circular DNA as a template and the following primers prepared based on the base sequence information on the acBGLB gene fragment. A 5' upstream region and a 3' downstream region of the acBGLB gene were obtained.

```
BGLB-inv-F:
                                    (SEQ ID NO: 10)
TAGGCGTTCGTTATGCGAAC BGLB-inv-R:
                                    (SEQ ID NO: 11)
AAACGAGATTCCAGATGGCG
```

The 5' upstream region and the 3' downstream region were analyzed by the method described in Example 3-(2). The full-length base sequence of the BGLB gene was determined.

Based on the base sequence obtained by the inverse PCR method, the following primers were prepared. PCR was performed using the genomic DNA as a template, to amplify the BGLB gene.

```
pBGLB-F:
                                    (SEQ ID NO: 12)
CTGGACCTATATTCCCCGAT pBGLB-R:
                                    (SEQ ID NO: 13)
TGGTTTGTCCATACTGCGTC
```

The DNA thus amplified was inserted into a pCR2.1-TOPO plasmid vector with TOPO TA cloning kit (manufactured by Invitrogen Corporation) to obtain a plasmid "pBGLB." An *Escherichia coli* TOP10 strain (manufactured by Invitrogen Corporation) was transformed with the obtained plasmid "pBGLB." Thereby, "*Escherichia coli* TOP10 strain/pBGLB" was obtained.

(4) Preparation of acBGLB cDNA and Intron Analysis of acBGLB Genomic DNA

An *Acremonium cellulolyticus* ACCP-5-1 strain was cultured in a cellulase induction medium at 32° C. for 2 days, and the fungal cells were collected by centrifugation. After frozen with liquid nitrogen, the resultant fungal cells were ground using a mortor and a pestle. The total RNA was isolated from the ground fungal cells with ISOGEN (Nippon Gene Co., Ltd.) in accordance with the protocol attached thereto. Further, a mRNA was purified from the total RNA with mRNA Purification Kit (Pharmacia Corporation) in accordance with the protocol attached thereto.

A cDNA was synthesized from the mRNA thus obtained with TimeSaver cDNA Synthesis Kit (Pharmacia Corporation) in accordance with the protocol attached thereto. The following primers containing the start codon and the stop codon were prepared from the acBGLB gene sequence, and PCR was performed using the cDNA as a template.

```
BGLB-N:
                                    (SEQ ID NO: 14)
ATGTATTCCGCATTTCTTTTGCTGC

BGLB-C:
                                    (SEQ ID NO: 15)
CTATTGTAGGCATTGAGAATACCAT
```

The base sequence (SEQ ID NO: 1) of the cDNA thus amplified was analyzed by the method described in Example 3-(2), and compared with the base sequence of the pBGLB genomic DNA. Thus, the positions of introns in the genomic DNA were determined.

(5) Estimation of Amino Acid Sequence of acBGLB

The exons and introns of the acBGLB genomic DNA isolated by the above-described method were composed of 2630 bp shown from positions 218 to 2847 of the base sequence of SEQ ID NO: 2. Moreover, the acBGLB genomic DNA contained three introns shown from the 734th to 792nd, 1665th to 1717th, and 2523rd to 2601st of the base sequence of SEQ ID NO: 2. The amino acid sequence of the acBGLB predicted from an open reading frame (ORF) was as shown in SEQ ID NO: 3. A part of the amino acid sequence predicted from the ORF corresponded to the internal sequence of the acBGLB determined in Example 2. This fact revealed that the isolated genomic DNA encoded the acBGLB. Note that, using signal sequence prediction software SignalP 3.0, the amino acid residues from −18 to −1 of the acBGLB were estimated to be a signal sequence.

Example 4

Expression of acBGLB Gene in *Trichoderma viride*

(1) Modification of acBGLB Gene Codon for Suitable Expression in *Trichoderma viride*

To express the acBGLB gene at a high level as an active protein in *Trichoderma viride*, the acBGLB gene was modified. As a result of trials and errors, a DNA comprising the base sequence of SEQ ID NO: 4 which was modified from the acBGLB gene by 13.2% or more of the bases was found out. In designing this modified acBGLB gene, 16 kinds of amino acids among 20 kinds of amino acids in the encoding base sequence were modified; in addition, the frequency distribution of codons used in *Trichoderma viride* was taken into consideration. This modified acBGLB gene was artificially synthesized by Gene Design Inc. In the artificial synthesis, the design was made such that XbaI and SnaBI were contained in a sequence upstream of the start codon, and that SalI and XbaI were contained downstream of the stop codon. Thus, a plasmid "pBGLBkai" was obtained in which the codon-modified acBGLB gene was inserted in XbaI of pUC19.

(2) Construction of Codon-Modified BGLB-Expression Plasmid BGLBkai-pCB1

The plasmid "pBGLBkai" was cleaved with SnaBI and SalI, and approximately 2.7 kbp of a gene fragment "BGLB-kai-N" was obtained. Meanwhile, to remove a hygromycin B resistance cassette from pCB1-Eg3X (International Publication No. WO98/11239), the pCB1-Eg3X was cleaved with a restriction enzyme XbaI, and then circularized again using TaKaRa DNA Ligation Kit Mighty Mix (manufactured by TAKARA SHUZO CO., LTD.). Thus, a plasmid "pCB1-Eg3X-hphless" was obtained. The "pCB1-Eg3X-hphless" was cleaved with StuI and XhoI, and approximately 7 kbp of a fragment was collected. To this, approximately 2.7 kbp of the gene fragment "BGLBkai-N" was ligated using TaKaRa DNA Ligation Kit Mighty Mix (manufactured by TAKARA SHUZO CO., LTD.). Thus, a plasmid "BGLBkai-pCB1" was prepared. The reaction conditions such as enzyme followed the conditions in the protocol attached to the kit. The plasmid "BGLBkai-pCB1" was constructed in such a manner as to express the modified acBGLB using the start codon of its own in the host *Trichoderma viride*.

(3) Preparation of *Trichoderma viride* Transformant with Plasmid "BGLBkai-pCB1"

*Trichoderma viride* was transformed with the plasmid "BGLBkai-pCB1" obtained in Example 4-(2) in accordance with the method described in International Publication No. WO2005/056787. The transformation was carried out by a co-transformation method using *Trichoderma viride* strain 2 deficient in a gene for uracil biosynthesis (pyr4) as a host and a pyr4 gene of *Neurospora crassa* as a selection marker. The *Trichoderma viride* strain 2 was cultured in 50 mL of a fungal cell-forming medium (1% yeast extract, 1% malt extract, 2% polypeptone, 2.5% glucose, 0.1% dipotassium hydrogen phosphate, 0.05% magnesium sulfate heptahydrate, 0.0001% uridine (pH7.0)) at 28° C. for 24 hours, and centrifuged at 3000 rpm for 10 minutes, and the fungal cells were collected. The obtained fungal cells were washed with 0.5 mol/L of sucrose, and suspended in a protoplast-forming enzyme solution (1 mg/mL of β-glucuronidase, 0.3 mg/mL of chitinase, 0.3 mg/mL of zymolyase, 0.5 mol/L of sucrose) that had been filtered through cotton. The mixture was shaken at 30° C. for 60 minutes, so that the hypha was formed into a protoplast. This suspension was filtered, and then centrifuged at 2500 rpm for 10 minutes to collect the protoplast, which was washed with a SUTC buffer (0.5 mol/L of sucrose, 10 mmol/L of calcium chloride, 10 mmol/L of Tris-HCl (pH 7.5)).

The protoplast was suspended in 100 μL of a SUTC buffer, to which 10 μg of a DNA solution 10 μL containing the plasmid "BGLBkai-pCB1" and 10 μL of a DNA solution containing the pyr4 gene were added. The resultant was allowed to stand in ice for 5 minutes. Next, 400 μl of a PEG solution (60% of PEG4000, 10 mmol/L of calcium chloride, 10 mmol/L of Tris-HCl (pH 7.5)) was added thereto, which was allowed to stand in ice for 20 minutes. Then, 10 mL of a SUTC buffer was added thereto, which was centrifuged at 2500 rpm for 10 minutes. The protoplast thus collected was suspended in 1 mL of a SUTC buffer, and each 200-μl solution of the protoplast suspension was overlaid with soft agar on a minimum medium containing 0.5 mol/L of sucrose, followed by culturing at 28° C. for 5 days. Subsequently, grown colonies were again transferred on a minimum medium. The colonies formed thereon were used as transformants.

(4) Culturing and Identification of "BGLBkai-pCB1" Transformant

The plasmid "BGLBkai-pCB1" was introduced into each of the minimum media. A line grown on the medium was selected, and cultured in accordance with WO 98/11239 A. The resultant culture supernatant fluid was separated by electrophoresis using 12% Gel SDS-PAGE mini (manufactured by TEFCO). A culture supernatant having a favorably detectable band which migrated the same distance as that of the acBGLB identified in Example 2 was selected.

(5) Identification of Partial Amino Acid Sequence of Recombinant Modified acBGLB To confirm that the protein expressed in a large amount in Example 4-(4) was the modified acBGLB, the partial amino acid sequence was determined. First, the protein in the culture supernatant was separated by electrophoresis using 12% Gel SDS-PAGE mini (manufactured by TEFCO). A band corresponding to the acBGLB separated according to the method in Example 2 was treated with lysyl endopeptidase. The degraded product was separated by electrophoresis using 12% Gel SDS-PAGE mini (manufactured by TEFCO), and blotted on a PVDF membrane (manufactured by Millipore Corporation). A band of the peptide fragment thus obtained was cut out. The N-terminal amino acid sequence of the peptide fragment was determined using a protein sequencer Model 492 (manufactured by Applied Biosystems Inc.). As a result, the N-terminal amino acid sequence corresponded to the partial amino acid sequence (SEQ ID NO: 6) of the acBGLB.

Example 5

Measurement of Enzyme Activity of *Trichoderma viride* Transformant

The β-glucosidase activity was measured using the culture supernatant of the "BGLBkai-pCB1" transformant obtained in Example 4-(4). The measurement method followed the method described in the literature (Methods in ENZYMOLOGY, vol. 160, Biomass Part A Cellulose and Hemicellulose, Willis A. Wood ed. p 109-110). Note that the β-glucosidase activity is defined as an activity of producing 1 μmol of p-nitrophenol from p-nitrophenyl-β-glucoside in 1 minute, and was represented as activity (U/mL) per mL of the culture supernatant. The result is as shown in Table 1. As apparent from Table 1, the transformant showed the activity approximately 7.5 times as high as a parental strain (original *Trichoderma viride* strain not deficient in a gene for uracil biosynthesis).

TABLE 1

| | β-glucosidase activity (U/mL) |
|---|---|
| Parental strain | 211 |
| Transformant | 1592 |

This revealed that a cellulase-producing microorganism having a low β-glucosidase activity over-expressed a β-glucosidase derived from *Acremonium cellulolyticus*, and that it was thus made possible to enhance the β-glucosidase activity of the microorganism.

INDUSTRIAL APPLICABILITY

As described above, the present invention makes it possible to obtain a β-glucosidase derived from *Acremonium cellulolyticus* as a purified protein or a cellulase preparation in high yield. By using the β-glucosidase or the cellulase preparation thus obtained, saccharification from biomass to glucose can be promoted, and treatments and modifications on a cellulose-based substrate can be carried out efficiently. Moreover, these β-glucosidase and cellulase preparation can be utilized at reduced cost. Further, by utilizing a filamentous fungus expressing a reduced amount of the β-glucosidase of the present invention, cellobiose useful as a sweetener, a cosmetic raw material, or a drug raw material can be produced efficiently.

The invention claimed is:

1. A protein comprising:
any one of the following (i) to (ii):
  (i) the amino acid sequence of SEQ ID NO: 3 but in which 1 to 8 amino acids are substituted, deleted, inserted and/or added;
  and
  (ii) the amino acid sequence of (i) from which a signal sequence is removed,
  provided that said protein has β-glucosidase activity and contains at least one amino acid insertion or substitution relative to the sequence of residues 1-795 of SEQ ID NO: 3, wherein said protein has been produced through being expressed from a filamentous fungus belonging to the genus *Trichoderma*.

2. The protein according to claim 1, which is a recombinant protein.

3. A cellulase preparation comprising a protein comprising any one of the following (i) to (ii):
  (i) the amino acid sequence of SEQ ID NO: 3 but in which 1 to 8 amino acids are substituted, deleted, inserted and/or added;
  and
  (ii) the amino acid sequence of (i) from which a signal sequence is removed,
  provided that said protein has β-glucosidase activity and contains at least one amino acid insertion or substitution relative to the sequence of residues 1-795 of SEQ ID NO: 3, wherein said protein has been produced through being expressed from a filamentous fungus belonging to the genus *Trichoderma*,
  and another protein, wherein the another protein is at least one protein selected from the group consisting of hemicellulase, endoglucanase, cellobiohydrolase, aminopeptidase, amylase, carbohydrase, carboxypeptidase, catalase, chitinase, cutinase, cyclodextrin glycosyltransferase, deoxyribonuclease, esterase, α-galactosidase, β-galactosidase, glucoamylase, α-glucosidase, haloperoxidase, invertase, laccase, lipase, mannosidase, oxidase, pectinase, peptide glutaminase, peroxidase, phytase, polyphenol oxidase, protease, ribonuclease, transglutaminase, and xylanase.

4. A detergent composition comprising a surfactant in admixture with a substance selected from any one of the following (a) to (b):
  (a) the protein according to claim 1, and
  (b) a cellulase preparation comprising a protein comprising any one of the following (i) to (ii) in admixture with another protein:
    (i) the amino acid sequence of SEQ ID NO: 3 but in which 1 to 8 amino acids are substituted, deleted, inserted and/or added;
    and
    (ii) the amino acid sequence of (i) from which a signal sequence is removed,
    provided that said protein has β-glucosidase activity and contains at least one amino acid insertion or substitution relative to the sequence of residues 1-795 of SEQ ID NO: 3, wherein said protein has been produced through being expressed from a filamentous fungus belonging to the genus *Trichoderma*,
    wherein the another protein is at least one protein selected from the group consisting of hemicellulase, endoglucanase, cellobiohydrolase, aminopeptidase, amylase, carbohydrase, carboxypeptidase, catalase, chitinase, cutinase, cyclodextrin glycosyltransferase, deoxyribonuclease, esterase, α-galactosidase, β-galactosidase, glucoamylase, α-glucosidase, haloperoxidase, invertase, laccase, lipase, mannosidase, oxidase, pectinase, peptide glutaminase, peroxidase, phytase, polyphenol oxidase, protease, ribonuclease, transglutaminase, and xylanase.

5. A method for degrading or converting a cellulose material, the method comprising the step of:

treating the cellulose material with a substance selected from any one of the following (a) to (b):
(a) the protein according to claim 1, and
(b) a cellulase preparation comprising a protein comprising any one of the following (i) to (ii) in admixture with another protein:
  (i) the amino acid sequence of SEQ ID NO: 3 but in which 1 to 8 amino acids are substituted, deleted, inserted and/or added; and
  (ii) the amino acid sequence of any (i) from which a signal sequence is removed,
provided that said protein has β-glucosidase activity and contains at least one amino acid insertion or substitution relative to the sequence of residues 1-795 of SEQ ID NO: 3, wherein said protein has been produced through being expressed from a filamentous fungus belonging to the genus *Trichoderma*,
wherein the another protein is at least one protein selected from the group consisting of hemicellulase, endoglucanase, cellobiohydrolase, aminopeptidase, amylase, carbohydrase, carboxypeptidase, catalase, chitinase, cutinase, cyclodextrin glycosyltransferase, deoxyribonuclease, esterase, α-galactosidase, β-galactosidase, glucoamylase, α-glucosidase, haloperoxidase, invertase, laccase, lipase, mannosidase, oxidase, pectinase, peptide glutaminase, peroxidase, phytase, polyphenol oxidase, protease, ribonuclease, transglutaminase, and xylanase.

6. A method for producing a degraded or converted cellulose material, the method comprising the steps of:
treating a cellulose material with a substance selected from any one of the following (a) to (b):
(a) the protein according to claim 1, and
(b) a cellulase preparation comprising a protein comprising any one of the following (i) to (ii) in admixture with another protein:
  (i) the amino acid sequence of SEQ ID NO: 3 but in which 1 to 8 amino acids are substituted, deleted, inserted and/or added; and
  (ii) the amino acid sequence of (i) from which a signal sequence is removed,
provided that said protein has β-glucosidase activity and contains at least one amino acid insertion or substitution relative to the sequence of residues 1-795 of SEQ ID NO: 3, wherein said protein has been produced through being expressed from a filamentous fungus belonging to the genus *Trichoderma*,
wherein the another protein is at least one protein selected from the group consisting of hemicellulase, endoglucanase, cellobiohydrolase, aminopeptidase, amylase, carbohydrase, carboxypeptidase, catalase, chitinase, cutinase, cyclodextrin glycosyltransferase, deoxyribonuclease, esterase, α-galactosidase, β-galactosidase, glucoamylase, α-glucosidase, haloperoxidase, invertase, laccase, lipase, mannosidase, oxidase, pectinase, peptide glutaminase, peroxidase, phytase, polyphenol oxidase, protease, ribonuclease, transglutaminase, and xylanase;
and collecting a degraded cellulose material.

7. The method according to claim 6, wherein the degraded cellulose material is a sugar.

8. A method for treating a cellulose-containing fiber, the method comprising the step of:
bringing a substance selected from any one of the following (a) to (d) into contact with the cellulose-containing fiber:
(a) the protein according to claim 1, and
(b) a cellulase preparation comprising a protein comprising any one of the following (i) to (ii) in admixture with another protein:
  (i) the amino acid sequence of SEQ ID NO: 3 but in which 1 to 8 amino acids are substituted, deleted, inserted and/or added; and
  (ii) the amino acid sequence of any (i) from which a signal sequence is removed,
provided that said protein has β-glucosidase activity and contains at least one amino acid insertion or substitution relative to the sequence of residues 1-795 of SEQ ID NO: 3, wherein said protein has been produced through being expressed from a filamentous fungus belonging to the genus *Trichoderma*,
(c) a detergent composition comprising a protein comprising any one of the following (i) to (ii) in admixture with a surfactant:
  (i) the amino acid sequence of SEQ ID NO: 3 but in which 1 to 8 amino acids are substituted, deleted, inserted and/or added; and
  (ii) the amino acid sequence of (i) from which a signal sequence is removed,
provided that said protein has β-glucosidase activity and contains at least one amino acid insertion or substitution relative to the sequence of residues 1-795 of SEQ ID NO: 3, wherein said protein has been produced through being expressed from a filamentous fungus belonging to the genus *Trichoderma*, and
(d) a detergent composition comprising a protein comprising any one of the following (i) to (ii) in admixture with another protein and a surfactant:
  (i) the amino acid sequence of SEQ ID NO: 3 but in which 1 to 8 amino acids are substituted, deleted, inserted and/or added; and
  (ii) the amino acid sequence of (i) from which a signal sequence is removed,
provided that said protein has β-glucosidase activity and contains at least one amino acid insertion or substitution relative to the sequence of residues 1-795 of SEQ ID NO: 3, wherein said protein has been produced through being expressed from a filamentous fungus belonging to the genus *Trichoderma*, and
wherein the another protein is at least one protein selected from the group consisting of hemicellulase, endoglucanase, cellobiohydrolase, aminopeptidase, amylase, carbohydrase, carboxypeptidase, catalase, chitinase, cutinase, cyclodextrin glycosyltransferase, deoxyribonuclease, esterase, α-galactosidase, β-galactosidase, glucoamylase, α-glucosidase, haloperoxidase, invertase, laccase, lipase, mannosidase, oxidase, pectinase, peptide glutaminase, peroxidase, phytase, polyphenol oxidase, protease, ribonuclease, transglutaminase, and xylanase.

9. A method for producing an animal feed having an improved digestibility, the method comprising the step of:

treating an animal feed with a substance selected from any one of the following (a) to (b):
(a) the protein according to claim 1, and
(b) a cellulase preparation comprising a protein comprising any one of the following (i) to (ii) in admixture with another protein:
  (i) the amino acid sequence of SEQ ID NO: 3 but in which 1 to 8 amino acids are substituted, deleted, inserted and/or added; and
  (ii) the amino acid sequence of (i) from which a signal sequence is removed,
provided that said protein has β-glucosidase activity and contains at least one amino acid insertion or substitution relative to the sequence of residues 1-795 of SEQ ID NO: 3, wherein said protein has been produced through being expressed from a filamentous fungus belonging to the genus *Trichoderma*,
wherein the another protein is at least one protein selected from the group consisting of hemicellulase, endoglucanase, cellobiohydrolase, aminopeptidase, amylase, carbohydrase, carboxypeptidase, catalase, chitinase, cutinase, cyclodextrin glycosyltransferase, deoxyribonuclease, esterase, α-galactosidase, β-galactosidase, glucoamylase, α-glucosidase, haloperoxidase, invertase, laccase, lipase, mannosidase, oxidase, pectinase, peptide glutaminase, peroxidase, phytase, polyphenol oxidase, protease, ribonuclease, transglutaminase, and xylanase.

* * * * *

SEQUENCE LISTING

```
<160> NUMBER OF SEQ ID NOS: 15

<210> SEQ ID NO 1
<211> LENGTH: 2442
<212> TYPE: DNA
<213> ORGANISM: Acremonium cellulolyticus
<220> FEATURE:
<221> NAME/KEY: sig_peptide
<222> LOCATION: (1)..(54)
<220> FEATURE:
<221> NAME/KEY: mat_peptide
<222> LOCATION: (55)..(2439)
<220> FEATURE:
<221> NAME/KEY: CDS
<222> LOCATION: (1)..(2439)

<400> SEQUENCE: 1 atg tat tcc gca ttt ctt ttg ctg ctg gct tcg gcc acg cct ata gtc      48
Met Tyr Ser Ala Phe Leu Leu Leu Leu Ala Ser Ala Thr Pro Ile Val
        -15                 -10                  -5 agc gcc cag tca gct tct tgg tcc gca gcc tac agt aaa gcc acg gct      96
Ser Ala Gln Ser Ala Ser Trp Ser Ala Ala Tyr Ser Lys Ala Thr Ala
 -1   1                5                    10 gct ttg agc aaa ctc tct caa aat gac aaa att ggt atg gtg aca ggc     144
Ala Leu Ser Lys Leu Ser Gln Asn Asp Lys Ile Gly Met Val Thr Gly
 15                  20                  25                  30 gtg gga tgg ggg aaa ggt cca tgt gtt gga aac act gcc gcg cca tct     192
Val Gly Trp Gly Lys Gly Pro Cys Val Gly Asn Thr Ala Ala Pro Ser
                 35                  40                  45 gga atc tcg ttt cca tca ctc tgt att caa gat agt ccc cta ggc gtt     240
Gly Ile Ser Phe Pro Ser Leu Cys Ile Gln Asp Ser Pro Leu Gly Val
             50                  55                  60 cgt tat gcg aac ccc gtc aca gcg ttt ccg gca ggc acg aat gct gga     288
Arg Tyr Ala Asn Pro Val Thr Ala Phe Pro Ala Gly Thr Asn Ala Gly
         65                  70                  75 atg acc tgg gat cgg acg ttg atg aac cag aga ggt gcc gct ctt ggt     336
Met Thr Trp Asp Arg Thr Leu Met Asn Gln Arg Gly Ala Ala Leu Gly
     80                  85                  90 gca gaa tcc aag ggg cta ggt gtc cat gtt cag tta ggg cct gtg gca     384
Ala Glu Ser Lys Gly Leu Gly Val His Val Gln Leu Gly Pro Val Ala
 95                 100                 105                 110 ggt ccc cta gga aag atc gcg cag ggt ggt cgt ggt tgg gaa gga ttt     432
Gly Pro Leu Gly Lys Ile Ala Gln Gly Gly Arg Gly Trp Glu Gly Phe
                115                 120                 125 gga acg gat cca tac ctc agt ggt gtt gct atg att gag act att tca     480
Gly Thr Asp Pro Tyr Leu Ser Gly Val Ala Met Ile Glu Thr Ile Ser
            130                 135                 140 ggt atg cag agt tcg ggt act cag gca tgc gcg aag cac tat att ggc     528
```

```
        Gly Met Gln Ser Ser Gly Thr Gln Ala Cys Ala Lys His Tyr Ile Gly
                    145                 150                 155 aac gag caa gag cta aac agg gaa tcg atg agt tct aat att gat gat              576
Asn Glu Gln Glu Leu Asn Arg Glu Ser Met Ser Ser Asn Ile Asp Asp
        160                 165                 170 cgt act ttg cac gag ctt tac ctg tgg ccc ttt gcc gat gcc gtc cgt              624
Arg Thr Leu His Glu Leu Tyr Leu Trp Pro Phe Ala Asp Ala Val Arg
175                 180                 185                 190 gcc aat gtt gcc agt gtg atg tgc tcc tac aac caa atc aat gga aca              672
Ala Asn Val Ala Ser Val Met Cys Ser Tyr Asn Gln Ile Asn Gly Thr
                195                 200                 205 ttt tcc tgt gag aat gaa gaa tcg atg aca ggt att ctg aag aca gag              720
Phe Ser Cys Glu Asn Glu Glu Ser Met Thr Gly Ile Leu Lys Thr Glu
        210                 215                 220 ctc ggc ttt cca gga tac ata atg tct gac tgg gat gca cag cac acc              768
Leu Gly Phe Pro Gly Tyr Ile Met Ser Asp Trp Asp Ala Gln His Thr
    225                 230                 235 aca gtt act agt gct aac tct gga ctt gat atg acg atg cca ggt agt              816
Thr Val Thr Ser Ala Asn Ser Gly Leu Asp Met Thr Met Pro Gly Ser
240                 245                 250 gat tat agt gat acg ccg agt agt gtc ctt tgg ggt caa aat ctg gcc              864
Asp Tyr Ser Asp Thr Pro Ser Ser Val Leu Trp Gly Gln Asn Leu Ala
255                 260                 265                 270 aat gcc atc tca agt ggc caa gtt gcc cag tcg cgt ctc gac gat atg              912
Asn Ala Ile Ser Ser Gly Gln Val Ala Gln Ser Arg Leu Asp Asp Met
                275                 280                 285 gtg act cga att ttg gct gct tgg tat ttg gtt ggg cag gat caa ggc              960
Val Thr Arg Ile Leu Ala Ala Trp Tyr Leu Val Gly Gln Asp Gln Gly
        290                 295                 300 ttc cct gcg gtg gcc ttt aac tct tgg acc ggt ggg caa gca agt gtt             1008
Phe Pro Ala Val Ala Phe Asn Ser Trp Thr Gly Gly Gln Ala Ser Val
    305                 310                 315 aat gtc aca tca aac cac aac caa gtt gcc cgt gca gtc gct cgc gat             1056
Asn Val Thr Ser Asn His Asn Gln Val Ala Arg Ala Val Ala Arg Asp
320                 325                 330 tct atc gtt ttg ctt aaa aat acc aat agc acg ctt ccg ttg aac aaa             1104
Ser Ile Val Leu Leu Lys Asn Thr Asn Ser Thr Leu Pro Leu Asn Lys
335                 340                 345                 350 cca tcg agc att gct att att ggc act gac gcc cag aca aac cct tcc             1152
Pro Ser Ser Ile Ala Ile Ile Gly Thr Asp Ala Gln Thr Asn Pro Ser
                355                 360                 365 ggg cca aac gct tgt act gat cgt ggt tgt gat act gga act ttg gct             1200
Gly Pro Asn Ala Cys Thr Asp Arg Gly Cys Asp Thr Gly Thr Leu Ala
        370                 375                 380 atg ggt tgg ggt agt gga act tgc caa ttt cca tat ctc aca gat cct             1248
Met Gly Trp Gly Ser Gly Thr Cys Gln Phe Pro Tyr Leu Thr Asp Pro
    385                 390                 395 cta aca gct att aaa act cga gct gcc agc gac ggg act acg atc acg             1296
Leu Thr Ala Ile Lys Thr Arg Ala Ala Ser Asp Gly Thr Thr Ile Thr
400                 405                 410 acg agc att agt gac aat ggc agt gcg gga gcc tca gtt gct caa agc             1344
Thr Ser Ile Ser Asp Asn Gly Ser Ala Gly Ala Ser Val Ala Gln Ser
415                 420                 425                 430 gcc gag tat gca atc gtt ttc atc aat tca gac tct ggc gaa ggg tac             1392
Ala Glu Tyr Ala Ile Val Phe Ile Asn Ser Asp Ser Gly Glu Gly Tyr
                435                 440                 445 ata aca gtc gaa ggc gtg gct ggt gac cgc aac aat ctc gac cca tgg             1440
Ile Thr Val Glu Gly Val Ala Gly Asp Arg Asn Asn Leu Asp Pro Trp
        450                 455                 460
```

-continued

| | | |
|---|---|---|
| cac agt ggc aat gca tta gtg caa tcc gtc gcc gca gtc aac aag aag<br>His Ser Gly Asn Ala Leu Val Gln Ser Val Ala Ala Val Asn Lys Lys<br>465 470 475 | 1488 |
| acg att gtc gtc att cat agc gtc ggg ccg gtc att ctt gaa acc ata<br>Thr Ile Val Val Ile His Ser Val Gly Pro Val Ile Leu Glu Thr Ile<br>480 485 490 | 1536 |
| ttg gcg caa cct aac gtt gtg gcc gta gta tgg gct ggc ata cca gga<br>Leu Ala Gln Pro Asn Val Val Ala Val Val Trp Ala Gly Ile Pro Gly<br>495 500 505 510 | 1584 |
| caa gag agc ggc tca gcc ctc acc gat att ctc tat ggg agt aca gct<br>Gln Glu Ser Gly Ser Ala Leu Thr Asp Ile Leu Tyr Gly Ser Thr Ala<br>515 520 525 | 1632 |
| ccc agt gga aag cta acg tac acg att gcc aaa cag gct tcc gat tac<br>Pro Ser Gly Lys Leu Thr Tyr Thr Ile Ala Lys Gln Ala Ser Asp Tyr<br>530 535 540 | 1680 |
| ggc act gca gtc gtc agt ggt agc gac aat tat cca gag gga ctt ttc<br>Gly Thr Ala Val Val Ser Gly Ser Asp Asn Tyr Pro Glu Gly Leu Phe<br>545 550 555 | 1728 |
| att gat tac cga cac ttc gac aaa agc aat att gaa cct cga tat gaa<br>Ile Asp Tyr Arg His Phe Asp Lys Ser Asn Ile Glu Pro Arg Tyr Glu<br>560 565 570 | 1776 |
| ttc ggc tat gga ctg tca tat aca acc ttt ggt tac acg aat ttg gca<br>Phe Gly Tyr Gly Leu Ser Tyr Thr Thr Phe Gly Tyr Thr Asn Leu Ala<br>575 580 585 590 | 1824 |
| att gat att acg gtt tcg acg ggc cca act act ggt caa ata gtt cct<br>Ile Asp Ile Thr Val Ser Thr Gly Pro Thr Thr Gly Gln Ile Val Pro<br>595 600 605 | 1872 |
| ggt gga cct tct gat ctt ttt gag tct gtt gga acc gtt acg gta cag<br>Gly Gly Pro Ser Asp Leu Phe Glu Ser Val Gly Thr Val Thr Val Gln<br>610 615 620 | 1920 |
| gtc gca aac aca ggc agc gtt gca ggc tca gaa gtt gca caa ctc tat<br>Val Ala Asn Thr Gly Ser Val Ala Gly Ser Glu Val Ala Gln Leu Tyr<br>625 630 635 | 1968 |
| att ggg ctg cca tcg tca gca ccg tca tca cca cca aaa cag ttg cgt<br>Ile Gly Leu Pro Ser Ser Ala Pro Ser Ser Pro Pro Lys Gln Leu Arg<br>640 645 650 | 2016 |
| ggg ttt gat aag ctt tct ctc gct gct ggc gct agc ggg acc gca acg<br>Gly Phe Asp Lys Leu Ser Leu Ala Ala Gly Ala Ser Gly Thr Ala Thr<br>655 660 665 670 | 2064 |
| ttc gat ttg aca cga aga gat ttg agt tac tgg gat gta tca aag cag<br>Phe Asp Leu Thr Arg Arg Asp Leu Ser Tyr Trp Asp Val Ser Lys Gln<br>675 680 685 | 2112 |
| aag tgg gtg gtt cca agc gga gca ttt acc gta tat gtt ggg gca tcg<br>Lys Trp Val Val Pro Ser Gly Ala Phe Thr Val Tyr Val Gly Ala Ser<br>690 695 700 | 2160 |
| agt agg gat att agg ttg cag ggg aca ttt acg ccc gga ggt agc tcg<br>Ser Arg Asp Ile Arg Leu Gln Gly Thr Phe Thr Pro Gly Gly Ser Ser<br>705 710 715 | 2208 |
| acc act tcg act ata act tcc tct aag act tct act act atc agc act<br>Thr Thr Ser Thr Ile Thr Ser Ser Lys Thr Ser Thr Thr Ile Ser Thr<br>720 725 730 | 2256 |
| tct gtt acc acc agt agc agt acg aca gct aaa acc acc aca act agc<br>Ser Val Thr Thr Ser Ser Ser Thr Thr Ala Lys Thr Thr Thr Thr Ser<br>735 740 745 750 | 2304 |
| tcg acc acg tca tct gcc ggg cca aca cag acc ccg tat gga cag tgt<br>Ser Thr Thr Ser Ser Ala Gly Pro Thr Gln Thr Pro Tyr Gly Gln Cys<br>755 760 765 | 2352 |
| ggt gga cag ggt tgg acc ggc cct aca gtg tgt tca tct ggc tgg act<br>Gly Gly Gln Gly Trp Thr Gly Pro Thr Val Cys Ser Ser Gly Trp Thr<br>770 775 780 | 2400 |

```
tgc aag gta acg aat caa tgg tat tct caa tgc cta caa tag         2442
Cys Lys Val Thr Asn Gln Trp Tyr Ser Gln Cys Leu Gln
        785                 790                 795

<210> SEQ ID NO 2
<211> LENGTH: 2990
<212> TYPE: DNA
<213> ORGANISM: Acremonium cellulolyticus
<220> FEATURE:
<221> NAME/KEY: sig_peptide
<222> LOCATION: (218)..(271)
<220> FEATURE:
<221> NAME/KEY: exon
<222> LOCATION: (218)..(733)
<220> FEATURE:
<221> NAME/KEY: CDS
<222> LOCATION: (218)..(733)
<220> FEATURE:
<221> NAME/KEY: Intron
<222> LOCATION: (734)..(792)
<220> FEATURE:
<221> NAME/KEY: exon
<222> LOCATION: (793)..(1664)
<220> FEATURE:
<221> NAME/KEY: CDS
<222> LOCATION: (793)..(1664)
<220> FEATURE:
<221> NAME/KEY: Intron
<222> LOCATION: (1665)..(1717)
<220> FEATURE:
<221> NAME/KEY: exon
<222> LOCATION: (1718)..(2522)
<220> FEATURE:
<221> NAME/KEY: CDS
<222> LOCATION: (1718)..(2522)
<220> FEATURE:
<221> NAME/KEY: Intron
<222> LOCATION: (2523)..(2601)
<220> FEATURE:
<221> NAME/KEY: exon
<222> LOCATION: (2602)..(2847)
<220> FEATURE:
<221> NAME/KEY: CDS
<222> LOCATION: (2602)..(2847)

<400> SEQUENCE: 2
ctggacctat attccccgat gaattatgga aagtgggtta catttcaagt tgaaatagct    60
tgcgtaaatg tttccattaa aaattataaa aagagacttt cttcagaaaa gtagattttg   120
gttgtgcaat tgagaaaggt tcatcgcaat cagtttgcaa gctgaagcca gaaccttaac   180
gatcacaggc attccctggt tttctggtct gacagga atg tat tcc gca ttt ctt    235
                                        Met Tyr Ser Ala Phe Leu
                                                        -15 ttg ctg ctg gct tcg gcc acg cct ata gtc agc gcc cag tca gct tct    283
Leu Leu Leu Ala Ser Ala Thr Pro Ile Val Ser Ala Gln Ser Ala Ser
    -10                 -5                   1 tgg tcc gca gcc tac agt aaa gcc acg gct gct ttg agc aaa ctc tct    331
Trp Ser Ala Ala Tyr Ser Lys Ala Thr Ala Ala Leu Ser Lys Leu Ser
5                   10                  15                  20 caa aat gac aaa att ggt atg gtg aca ggc gtg gga tgg ggg aaa ggt    379
Gln Asn Asp Lys Ile Gly Met Val Thr Gly Val Gly Trp Gly Lys Gly
                25                  30                  35 cca tgt gtt gga aac act gcc gcg cca tct gga atc tcg ttt cca tca    427
Pro Cys Val Gly Asn Thr Ala Ala Pro Ser Gly Ile Ser Phe Pro Ser
            40                  45                  50 ctc tgt att caa gat agt ccc cta ggc gtt cgt tat gcg aac ccc gtc    475
Leu Cys Ile Gln Asp Ser Pro Leu Gly Val Arg Tyr Ala Asn Pro Val
        55                  60                  65
```

|   |   |   |   |   |   |   |   |   |   |   |   |   |   |   |   |     |
|---|---|---|---|---|---|---|---|---|---|---|---|---|---|---|---|-----|
| aca | gcg | ttt | ccg | gca | ggc | acg | aat | gct | gga | atg | acc | tgg | gat | cgg | acg | 523 |
| Thr | Ala | Phe | Pro | Ala | Gly | Thr | Asn | Ala | Gly | Met | Thr | Trp | Asp | Arg | Thr |     |
|     | 70  |     |     |     | 75  |     |     |     | 80  |     |     |     |     |     |     |     |

|   |   |   |   |   |   |   |   |   |   |   |   |   |   |   |   |     |
|---|---|---|---|---|---|---|---|---|---|---|---|---|---|---|---|-----|
| ttg | atg | aac | cag | aga | ggt | gcc | gct | ctt | ggt | gca | gaa | tcc | aag | ggg | cta | 571 |
| Leu | Met | Asn | Gln | Arg | Gly | Ala | Ala | Leu | Gly | Ala | Glu | Ser | Lys | Gly | Leu |     |
| 85  |     |     |     | 90  |     |     |     | 95  |     |     |     | 100 |     |     |     |     |

|   |   |   |   |   |   |   |   |   |   |   |   |   |   |   |   |     |
|---|---|---|---|---|---|---|---|---|---|---|---|---|---|---|---|-----|
| ggt | gtc | cat | gtt | cag | tta | ggg | cct | gtg | gca | ggt | ccc | cta | gga | aag | atc | 619 |
| Gly | Val | His | Val | Gln | Leu | Gly | Pro | Val | Ala | Gly | Pro | Leu | Gly | Lys | Ile |     |
|     |     |     |     | 105 |     |     |     | 110 |     |     |     | 115 |     |     |     |     |

|   |   |   |   |   |   |   |   |   |   |   |   |   |   |   |   |     |
|---|---|---|---|---|---|---|---|---|---|---|---|---|---|---|---|-----|
| gcg | cag | ggt | ggt | cgt | ggt | tgg | gaa | gga | ttt | gga | acg | gat | cca | tac | ctc | 667 |
| Ala | Gln | Gly | Gly | Arg | Gly | Trp | Glu | Gly | Phe | Gly | Thr | Asp | Pro | Tyr | Leu |     |
|     |     |     | 120 |     |     |     | 125 |     |     |     | 130 |     |     |     |     |     |

|   |   |   |   |   |   |   |   |   |   |   |   |   |   |   |   |     |
|---|---|---|---|---|---|---|---|---|---|---|---|---|---|---|---|-----|
| agt | ggt | gtt | gct | atg | att | gag | act | att | tca | ggt | atg | cag | agt | tcg | ggt | 715 |
| Ser | Gly | Val | Ala | Met | Ile | Glu | Thr | Ile | Ser | Gly | Met | Gln | Ser | Ser | Gly |     |
|     |     |     | 135 |     |     |     | 140 |     |     |     | 145 |     |     |     |     |     |

|   |   |   |   |   |   |   |   |   |   |     |
|---|---|---|---|---|---|---|---|---|---|-----|
| act | cag | gca | tgc | gcg | aag | gtgtgtatat | ctccgcgaag | gaaacccgta |  | 763 |
| Thr | Gln | Ala | Cys | Ala | Lys |  |  |  |  |     |
|     | 150 |     |     |     |     |  |  |  |  |     |

|   |   |   |   |   |   |   |   |   |   |   |     |
|---|---|---|---|---|---|---|---|---|---|---|-----|
| aataagaatg | atctaatgaa | ccctgtcag | cac | tat | att | ggc | aac | gag | caa | gag | 816 |
|  |  |  | His | Tyr | Ile | Gly | Asn | Glu | Gln | Glu |     |
|  |  |  |     |     | 155 |     |     |     | 160 |     |     |

|   |   |   |   |   |   |   |   |   |   |   |   |   |   |   |   |     |
|---|---|---|---|---|---|---|---|---|---|---|---|---|---|---|---|-----|
| cta | aac | agg | gaa | tcg | atg | agt | tct | aat | att | gat | gat | cgt | act | ttg | cac | 864 |
| Leu | Asn | Arg | Glu | Ser | Met | Ser | Ser | Asn | Ile | Asp | Asp | Arg | Thr | Leu | His |     |
|     |     |     | 165 |     |     |     | 170 |     |     |     | 175 |     |     |     |     |     |

|   |   |   |   |   |   |   |   |   |   |   |   |   |   |   |   |     |
|---|---|---|---|---|---|---|---|---|---|---|---|---|---|---|---|-----|
| gag | ctt | tac | ctg | tgg | ccc | ttt | gcc | gat | gcc | gtc | cgt | gcc | aat | gtt | gcc | 912 |
| Glu | Leu | Tyr | Leu | Trp | Pro | Phe | Ala | Asp | Ala | Val | Arg | Ala | Asn | Val | Ala |     |
|     | 180 |     |     |     | 185 |     |     |     | 190 |     |     |     |     |     |     |     |

|   |   |   |   |   |   |   |   |   |   |   |   |   |   |   |   |     |
|---|---|---|---|---|---|---|---|---|---|---|---|---|---|---|---|-----|
| agt | gtg | atg | tgc | tcc | tac | aac | caa | atc | aat | gga | aca | ttt | tcc | tgt | gag | 960 |
| Ser | Val | Met | Cys | Ser | Tyr | Asn | Gln | Ile | Asn | Gly | Thr | Phe | Ser | Cys | Glu |     |
| 195 |     |     |     | 200 |     |     |     | 205 |     |     |     | 210 |     |     |     |     |

|   |   |   |   |   |   |   |   |   |   |   |   |   |   |   |   |     |
|---|---|---|---|---|---|---|---|---|---|---|---|---|---|---|---|-----|
| aat | gaa | gaa | tcg | atg | aca | ggt | att | ctg | aag | aca | gag | ctc | ggc | ttt | cca | 1008 |
| Asn | Glu | Glu | Ser | Met | Thr | Gly | Ile | Leu | Lys | Thr | Glu | Leu | Gly | Phe | Pro |     |
|     |     |     | 215 |     |     |     | 220 |     |     |     | 225 |     |     |     |     |     |

|   |   |   |   |   |   |   |   |   |   |   |   |   |   |   |   |     |
|---|---|---|---|---|---|---|---|---|---|---|---|---|---|---|---|-----|
| gga | tac | ata | atg | tct | gac | tgg | gat | gca | cag | cac | acc | aca | gtt | act | agt | 1056 |
| Gly | Tyr | Ile | Met | Ser | Asp | Trp | Asp | Ala | Gln | His | Thr | Thr | Val | Thr | Ser |     |
|     |     |     | 230 |     |     |     | 235 |     |     |     | 240 |     |     |     |     |     |

|   |   |   |   |   |   |   |   |   |   |   |   |   |   |   |   |     |
|---|---|---|---|---|---|---|---|---|---|---|---|---|---|---|---|-----|
| gct | aac | tct | gga | ctt | gat | atg | acg | atg | cca | ggt | agt | gat | tat | agt | gat | 1104 |
| Ala | Asn | Ser | Gly | Leu | Asp | Met | Thr | Met | Pro | Gly | Ser | Asp | Tyr | Ser | Asp |     |
|     |     | 245 |     |     |     | 250 |     |     |     | 255 |     |     |     |     |     |     |

|   |   |   |   |   |   |   |   |   |   |   |   |   |   |   |   |     |
|---|---|---|---|---|---|---|---|---|---|---|---|---|---|---|---|-----|
| acg | ccg | agt | agt | gtc | ctt | tgg | ggt | caa | aat | ctg | gcc | aat | gcc | atc | tca | 1152 |
| Thr | Pro | Ser | Ser | Val | Leu | Trp | Gly | Gln | Asn | Leu | Ala | Asn | Ala | Ile | Ser |     |
|     | 260 |     |     |     | 265 |     |     |     | 270 |     |     |     |     |     |     |     |

|   |   |   |   |   |   |   |   |   |   |   |   |   |   |   |   |     |
|---|---|---|---|---|---|---|---|---|---|---|---|---|---|---|---|-----|
| agt | ggc | caa | gtt | gcc | cag | tcg | cgt | ctc | gac | gat | atg | gtg | act | cga | att | 1200 |
| Ser | Gly | Gln | Val | Ala | Gln | Ser | Arg | Leu | Asp | Asp | Met | Val | Thr | Arg | Ile |     |
| 275 |     |     |     | 280 |     |     |     | 285 |     |     |     | 290 |     |     |     |     |

|   |   |   |   |   |   |   |   |   |   |   |   |   |   |   |   |     |
|---|---|---|---|---|---|---|---|---|---|---|---|---|---|---|---|-----|
| ttg | gct | gct | tgg | tat | ttg | gtt | ggg | cag | gat | caa | ggc | ttc | cct | gcg | gtg | 1248 |
| Leu | Ala | Ala | Trp | Tyr | Leu | Val | Gly | Gln | Asp | Gln | Gly | Phe | Pro | Ala | Val |     |
|     |     |     | 295 |     |     |     | 300 |     |     |     | 305 |     |     |     |     |     |

|   |   |   |   |   |   |   |   |   |   |   |   |   |   |   |   |     |
|---|---|---|---|---|---|---|---|---|---|---|---|---|---|---|---|-----|
| gcc | ttt | aac | tct | tgg | acc | ggt | ggg | caa | gca | agt | gtt | aat | gtc | aca | tca | 1296 |
| Ala | Phe | Asn | Ser | Trp | Thr | Gly | Gly | Gln | Ala | Ser | Val | Asn | Val | Thr | Ser |     |
|     |     |     | 310 |     |     |     | 315 |     |     |     | 320 |     |     |     |     |     |

|   |   |   |   |   |   |   |   |   |   |   |   |   |   |   |   |     |
|---|---|---|---|---|---|---|---|---|---|---|---|---|---|---|---|-----|
| aac | cac | aac | caa | gtt | gcc | cgt | gca | gtc | gct | cgc | gat | tct | atc | gtt | ttg | 1344 |
| Asn | His | Asn | Gln | Val | Ala | Arg | Ala | Val | Ala | Arg | Asp | Ser | Ile | Val | Leu |     |
|     | 325 |     |     |     | 330 |     |     |     | 335 |     |     |     |     |     |     |     |

|   |   |   |   |   |   |   |   |   |   |   |   |   |   |   |   |     |
|---|---|---|---|---|---|---|---|---|---|---|---|---|---|---|---|-----|
| ctt | aaa | aat | acc | aat | agc | acg | ctt | ccg | ttg | aac | aaa | cca | tcg | agc | att | 1392 |
| Leu | Lys | Asn | Thr | Asn | Ser | Thr | Leu | Pro | Leu | Asn | Lys | Pro | Ser | Ser | Ile |     |
|     | 340 |     |     |     | 345 |     |     |     | 350 |     |     |     |     |     |     |     |

|   |   |   |   |   |   |   |   |   |   |   |   |   |   |   |   |     |
|---|---|---|---|---|---|---|---|---|---|---|---|---|---|---|---|-----|
| gct | att | att | ggc | act | gac | gcc | cag | aca | aac | cct | tcc | ggg | cca | aac | gct | 1440 |
| Ala | Ile | Ile | Gly | Thr | Asp | Ala | Gln | Thr | Asn | Pro | Ser | Gly | Pro | Asn | Ala |     |
| 355 |     |     |     | 360 |     |     |     | 365 |     |     |     | 370 |     |     |     |     |

```
tgt act gat cgt ggt tgt gat act gga act ttg gct atg ggt tgg ggt    1488
Cys Thr Asp Arg Gly Cys Asp Thr Gly Thr Leu Ala Met Gly Trp Gly
            375                 380                 385 agt gga act tgc caa ttt cca tat ctc aca gat cct cta aca gct att    1536
Ser Gly Thr Cys Gln Phe Pro Tyr Leu Thr Asp Pro Leu Thr Ala Ile
            390                 395                 400 aaa act cga gct gcc agc gac ggg act acg atc acg acg agc att agt    1584
Lys Thr Arg Ala Ala Ser Asp Gly Thr Thr Ile Thr Thr Ser Ile Ser
            405                 410                 415 gac aat ggc agt gcg gga gcc tca gtt gct caa agc gcc gag tat gca    1632
Asp Asn Gly Ser Ala Gly Ala Ser Val Ala Gln Ser Ala Glu Tyr Ala
            420                 425                 430 atc gtt ttc atc aat tca gac tct ggc gaa gg gtaagtgcct gacatctttt    1684
Ile Val Phe Ile Asn Ser Asp Ser Gly Glu Gly
435                 440                 445 tttcgccgtt ggcatcataa taacgaaaat tag g tac ata aca gtc gaa ggc     1736
                                      Tyr Ile Thr Val Glu Gly
                                                          450 gtc gct ggt gac cgc aac aat ctc gac cca tgg cac agt ggc aat gca    1784
Val Ala Gly Asp Arg Asn Asn Leu Asp Pro Trp His Ser Gly Asn Ala
            455                 460                 465 tta gtg caa tcc gtc gcc gca gtc aac aag aag acg att gtc gtc att    1832
Leu Val Gln Ser Val Ala Ala Val Asn Lys Lys Thr Ile Val Val Ile
            470                 475                 480 cat agc gtc ggg ccg gtc att ctt gaa acc ata ttg gcg caa cct aac    1880
His Ser Val Gly Pro Val Ile Leu Glu Thr Ile Leu Ala Gln Pro Asn
            485                 490                 495 gtt gtg gcc gta gta tgg gct ggc ata cca gga caa gag agc ggc tca    1928
Val Val Ala Val Val Trp Ala Gly Ile Pro Gly Gln Glu Ser Gly Ser
500                 505                 510                 515 gcc ctc acc gat att ctc tat ggg agt aca gct ccc agt gga aag cta    1976
Ala Leu Thr Asp Ile Leu Tyr Gly Ser Thr Ala Pro Ser Gly Lys Leu
            520                 525                 530 acg tac acg att gcc aaa cag gct tcc gat tac ggc act gca gtc gtc    2024
Thr Tyr Thr Ile Ala Lys Gln Ala Ser Asp Tyr Gly Thr Ala Val Val
            535                 540                 545 agt ggt agc gac aat tat cca gag gga ctt ttc att gat tac cga cac    2072
Ser Gly Ser Asp Asn Tyr Pro Glu Gly Leu Phe Ile Asp Tyr Arg His
            550                 555                 560 ttc gac aaa agc aat att gaa cct cga tat gaa ttc ggc tat gga ctg    2120
Phe Asp Lys Ser Asn Ile Glu Pro Arg Tyr Glu Phe Gly Tyr Gly Leu
            565                 570                 575 tca tat aca acc ttt ggt tac acg aat ttg gca att gat att acg gtt    2168
Ser Tyr Thr Thr Phe Gly Tyr Thr Asn Leu Ala Ile Asp Ile Thr Val
580                 585                 590                 595 tcg acg ggc cca act act ggt caa ata gtt cct ggt gga cct tct gat    2216
Ser Thr Gly Pro Thr Thr Gly Gln Ile Val Pro Gly Gly Pro Ser Asp
            600                 605                 610 ctt ttt gag tct gtt gga acc gtt acg gta cag gtc gca aac aca ggc    2264
Leu Phe Glu Ser Val Gly Thr Val Thr Val Gln Val Ala Asn Thr Gly
            615                 620                 625 agc gtt gca ggc tca gaa gtt gca caa ctc tat att ggg ctg cca tcg    2312
Ser Val Ala Gly Ser Glu Val Ala Gln Leu Tyr Ile Gly Leu Pro Ser
            630                 635                 640 tca gca ccg tca tca cca cca aaa cag ttg cgt ggg ttt gat aag ctt    2360
Ser Ala Pro Ser Ser Pro Pro Lys Gln Leu Arg Gly Phe Asp Lys Leu
            645                 650                 655 tct ctc gct gct ggc gct agc ggg acc gca acg ttc gat ttg aca cga    2408
Ser Leu Ala Ala Gly Ala Ser Gly Thr Ala Thr Phe Asp Leu Thr Arg
```

```
                660             665             670             675
aga gat ttg agt tac tgg gat gta tca aag cag aag tgg gtg gtt cca         2456
Arg Asp Leu Ser Tyr Trp Asp Val Ser Lys Gln Lys Trp Val Val Pro
            680             685             690 agc gga gca ttt acc gta tat gtt ggg gca tcg agt agg gat att agg         2504
Ser Gly Ala Phe Thr Val Tyr Val Gly Ala Ser Ser Arg Asp Ile Arg
            695             700             705 ttg cag ggg aca ttt acg gtaggttgac tattatgagt cctatgtatc                2552
Leu Gln Gly Thr Phe Thr
            710 gtcaacgatg agatttaaat caggtgagcc gatgctgacc gtggttaag ccc gga ggt       2610
                                                     Pro Gly Gly
                                                             715 agc tcg acc act tcg act ata act tcc tct aag act tct act act atc         2658
Ser Ser Thr Thr Ser Thr Ile Thr Ser Ser Lys Thr Ser Thr Thr Ile
            720             725             730 agc act tct gtt acc acc agt agc agt acg aca gct aaa acc acc aca         2706
Ser Thr Ser Val Thr Thr Ser Ser Ser Thr Thr Ala Lys Thr Thr Thr
            735             740             745 act agc tcg acc acg tca tct gcc ggg cca aca cag acc ccg tat gga         2754
Thr Ser Ser Thr Thr Ser Ser Ala Gly Pro Thr Gln Thr Pro Tyr Gly
            750             755             760 cag tgt ggt gga cag ggt tgg acc ggc cct aca gtg tgt tca tct ggc         2802
Gln Cys Gly Gly Gln Gly Trp Thr Gly Pro Thr Val Cys Ser Ser Gly
765             770             775             780 tgg act tgc aag gta acg aat caa tgg tat tct caa tgc cta caa             2847
Trp Thr Cys Lys Val Thr Asn Gln Trp Tyr Ser Gln Cys Leu Gln
            785             790             795 taggttcaat gtacagatta acatttagtg ggaatgaatc aaaaattggt ttgtgttcat       2907
taatacatag acacagagag cgattcgata ctgtacatag tggtatcctg aatatcgggt       2967
caggacgcag tatggacaaa cca                                               2990

<210> SEQ ID NO 3
<211> LENGTH: 813
<212> TYPE: PRT
<213> ORGANISM: Acremonium cellulolyticus

<400> SEQUENCE: 3

Met Tyr Ser Ala Phe Leu Leu Leu Ala Ser Ala Thr Pro Ile Val
            -15             -10             -5

Ser Ala Gln Ser Ala Ser Trp Ser Ala Ala Tyr Ser Lys Ala Thr Ala
    -1   1           5                   10

Ala Leu Ser Lys Leu Ser Gln Asn Asp Lys Ile Gly Met Val Thr Gly
15                  20                  25                  30

Val Gly Trp Gly Lys Gly Pro Cys Val Gly Asn Thr Ala Ala Pro Ser
                35                  40                  45

Gly Ile Ser Phe Pro Ser Leu Cys Ile Gln Asp Ser Pro Leu Gly Val
            50                  55                  60

Arg Tyr Ala Asn Pro Val Thr Ala Phe Pro Ala Gly Thr Asn Ala Gly
            65                  70                  75

Met Thr Trp Asp Arg Thr Leu Met Asn Gln Arg Gly Ala Ala Leu Gly
80                  85                  90

Ala Glu Ser Lys Gly Leu Gly Val His Val Gln Leu Gly Pro Val Ala
95                  100                 105                 110

Gly Pro Leu Gly Lys Ile Ala Gln Gly Gly Arg Gly Trp Glu Gly Phe
                115                 120                 125
```

```
Gly Thr Asp Pro Tyr Leu Ser Gly Val Ala Met Ile Glu Thr Ile Ser
            130                 135                 140

Gly Met Gln Ser Ser Gly Thr Gln Ala Cys Ala Lys His Tyr Ile Gly
            145                 150                 155

Asn Glu Gln Glu Leu Asn Arg Glu Ser Met Ser Ser Asn Ile Asp Asp
            160                 165                 170

Arg Thr Leu His Glu Leu Tyr Leu Trp Pro Phe Ala Asp Ala Val Arg
175                 180                 185                 190

Ala Asn Val Ala Ser Val Met Cys Ser Tyr Asn Gln Ile Asn Gly Thr
                195                 200                 205

Phe Ser Cys Glu Asn Glu Glu Ser Met Thr Gly Ile Leu Lys Thr Glu
            210                 215                 220

Leu Gly Phe Pro Gly Tyr Ile Met Ser Asp Trp Asp Ala Gln His Thr
            225                 230                 235

Thr Val Thr Ser Ala Asn Ser Gly Leu Asp Met Thr Met Pro Gly Ser
            240                 245                 250

Asp Tyr Ser Asp Thr Pro Ser Ser Val Leu Trp Gly Gln Asn Leu Ala
255                 260                 265                 270

Asn Ala Ile Ser Ser Gly Gln Val Ala Gln Ser Arg Leu Asp Asp Met
                275                 280                 285

Val Thr Arg Ile Leu Ala Ala Trp Tyr Leu Val Gly Gln Asp Gln Gly
            290                 295                 300

Phe Pro Ala Val Ala Phe Asn Ser Trp Thr Gly Gly Gln Ala Ser Val
            305                 310                 315

Asn Val Thr Ser Asn His Asn Gln Val Ala Arg Ala Val Ala Arg Asp
320                 325                 330

Ser Ile Val Leu Leu Lys Asn Thr Asn Ser Thr Leu Pro Leu Asn Lys
335                 340                 345                 350

Pro Ser Ser Ile Ala Ile Gly Thr Asp Ala Gln Thr Asn Pro Ser
                355                 360                 365

Gly Pro Asn Ala Cys Thr Asp Arg Gly Cys Asp Thr Gly Thr Leu Ala
            370                 375                 380

Met Gly Trp Gly Ser Gly Thr Cys Gln Phe Pro Tyr Leu Thr Asp Pro
            385                 390                 395

Leu Thr Ala Ile Lys Thr Arg Ala Ala Ser Asp Gly Thr Thr Ile Thr
400                 405                 410

Thr Ser Ile Ser Asp Asn Gly Ser Ala Gly Ala Ser Val Ala Gln Ser
415                 420                 425                 430

Ala Glu Tyr Ala Ile Val Phe Ile Asn Ser Asp Ser Gly Glu Gly Tyr
                435                 440                 445

Ile Thr Val Glu Gly Val Ala Gly Asp Arg Asn Asn Leu Asp Pro Trp
            450                 455                 460

His Ser Gly Asn Ala Leu Val Gln Ser Val Ala Ala Val Asn Lys Lys
            465                 470                 475

Thr Ile Val Val Ile His Ser Val Gly Pro Val Ile Leu Glu Thr Ile
            480                 485                 490

Leu Ala Gln Pro Asn Val Val Ala Val Val Trp Ala Gly Ile Pro Gly
495                 500                 505                 510

Gln Glu Ser Gly Ser Ala Leu Thr Asp Ile Leu Tyr Gly Ser Thr Ala
                515                 520                 525

Pro Ser Gly Lys Leu Thr Tyr Thr Ile Ala Lys Gln Ala Ser Asp Tyr
            530                 535                 540

Gly Thr Ala Val Val Ser Gly Ser Asp Asn Tyr Pro Glu Gly Leu Phe
```

-continued

```
                545                 550                 555
Ile Asp Tyr Arg His Phe Asp Lys Ser Asn Ile Glu Pro Arg Tyr Glu
560                 565                 570

Phe Gly Tyr Gly Leu Ser Tyr Thr Thr Phe Gly Tyr Thr Asn Leu Ala
575                 580                 585                 590

Ile Asp Ile Thr Val Ser Thr Gly Pro Thr Thr Gly Gln Ile Val Pro
                595                 600                 605

Gly Gly Pro Ser Asp Leu Phe Glu Ser Val Gly Thr Val Thr Val Gln
                610                 615                 620

Val Ala Asn Thr Gly Ser Val Ala Gly Ser Glu Val Ala Gln Leu Tyr
                625                 630                 635

Ile Gly Leu Pro Ser Ser Ala Pro Ser Ser Pro Lys Gln Leu Arg
640                 645                 650

Gly Phe Asp Lys Leu Ser Leu Ala Ala Gly Ala Ser Gly Thr Ala Thr
655                 660                 665                 670

Phe Asp Leu Thr Arg Arg Asp Leu Ser Tyr Trp Asp Val Ser Lys Gln
                675                 680                 685

Lys Trp Val Val Pro Ser Gly Ala Phe Thr Val Tyr Val Gly Ala Ser
                690                 695                 700

Ser Arg Asp Ile Arg Leu Gln Gly Thr Phe Thr Pro Gly Gly Ser Ser
                705                 710                 715

Thr Thr Ser Thr Ile Thr Ser Ser Lys Thr Ser Thr Ile Ser Thr
720                 725                 730

Ser Val Thr Thr Ser Ser Ser Thr Thr Ala Lys Thr Thr Thr Thr Ser
735                 740                 745                 750

Ser Thr Thr Ser Ser Ala Gly Pro Thr Gln Thr Pro Tyr Gly Gln Cys
                755                 760                 765

Gly Gly Gln Gly Trp Thr Gly Pro Thr Val Cys Ser Ser Gly Trp Thr
                770                 775                 780

Cys Lys Val Thr Asn Gln Trp Tyr Ser Gln Cys Leu Gln
785                 790                 795

<210> SEQ ID NO 4
<211> LENGTH: 2442
<212> TYPE: DNA
<213> ORGANISM: Acremonium cellulolyticus
<220> FEATURE:
<221> NAME/KEY: sig_peptide
<222> LOCATION: (1)..(54)
<220> FEATURE:
<221> NAME/KEY: mat_peptide
<222> LOCATION: (55)..(2439)
<220> FEATURE:
<221> NAME/KEY: CDS
<222> LOCATION: (1)..(2439)

<400> SEQUENCE: 4 atg tac tcc gcc ttc ctt ttg ctg ctg gct tcg gcc acc cct atc gtc    48
Met Tyr Ser Ala Phe Leu Leu Leu Ala Ser Ala Thr Pro Ile Val
            -15                 -10                  -5 agc gcc cag tcc gct tct tgg tcc gcc gcc tac tcc aag gcc acc gct    96
Ser Ala Gln Ser Ala Ser Trp Ser Ala Ala Tyr Ser Lys Ala Thr Ala
 -1   1               5                  10 gct ttg agc aag ctc tct cag aac gac aag atc ggt atg gtg acc ggc   144
Ala Leu Ser Lys Leu Ser Gln Asn Asp Lys Ile Gly Met Val Thr Gly
 15                  20                  25                  30 gtg gga tgg ggt aag ggt ccc tgc gtt gga aac act gcc gcg ccc tct   192
Val Gly Trp Gly Lys Gly Pro Cys Val Gly Asn Thr Ala Ala Pro Ser
                 35                  40                  45
```

```
gga atc tcg ttc ccc tcc ctc tgc atc cag gat tcc ccc ctc ggc gtt      240
Gly Ile Ser Phe Pro Ser Leu Cys Ile Gln Asp Ser Pro Leu Gly Val
            50                  55                  60 cgt tac gcg aac ccc gtc acc gcg ttc ccc gcc ggc acc aac gct gga      288
Arg Tyr Ala Asn Pro Val Thr Ala Phe Pro Ala Gly Thr Asn Ala Gly
        65                  70                  75 atg acc tgg gat cgc acc ttg atg aac cag cgc ggt gcc gct ctt ggt      336
Met Thr Trp Asp Arg Thr Leu Met Asn Gln Arg Gly Ala Ala Leu Gly
    80                  85                  90 gcc gaa tcc aag ggt ctc ggt gtc cac gtt cag ctc ggt cct gtg gcc      384
Ala Glu Ser Lys Gly Leu Gly Val His Val Gln Leu Gly Pro Val Ala
95                  100                 105                 110 ggt ccc ctc gga aag atc gcg cag ggt ggt cgt ggt tgg gaa gga ttc      432
Gly Pro Leu Gly Lys Ile Ala Gln Gly Gly Arg Gly Trp Glu Gly Phe
                115                 120                 125 gga acc gat ccc tac ctc tcc ggt gtt gct atg att gag act att tcc      480
Gly Thr Asp Pro Tyr Leu Ser Gly Val Ala Met Ile Glu Thr Ile Ser
            130                 135                 140 ggt atg cag tcc tcg ggt act cag gcc tgc gcg aag cac tac att ggc      528
Gly Met Gln Ser Ser Gly Thr Gln Ala Cys Ala Lys His Tyr Ile Gly
        145                 150                 155 aac gag cag gag ctc aac cgc gaa tcg atg tcc tct aac att gat gat      576
Asn Glu Gln Glu Leu Asn Arg Glu Ser Met Ser Ser Asn Ile Asp Asp
    160                 165                 170 cgt act ttg cac gag ctt tac ctg tgg ccc ttc gcc gat gcc gtc cgt      624
Arg Thr Leu His Glu Leu Tyr Leu Trp Pro Phe Ala Asp Ala Val Arg
175                 180                 185                 190 gcc aac gtt gcc tcc gtg atg tgc tcc tac aac cag atc aac gga acc      672
Ala Asn Val Ala Ser Val Met Cys Ser Tyr Asn Gln Ile Asn Gly Thr
                195                 200                 205 ttc tcc tgc gag aac gaa gaa tcg atg acc ggt att ctg aag acc gag      720
Phe Ser Cys Glu Asn Glu Glu Ser Met Thr Gly Ile Leu Lys Thr Glu
            210                 215                 220 ctc ggc ttc ccc gga tac atc atg tct gac tgg gat gcc cag cac acc      768
Leu Gly Phe Pro Gly Tyr Ile Met Ser Asp Trp Asp Ala Gln His Thr
        225                 230                 235 acc gtt act tcc gct aac tct gga ctt gat atg acc atg ccc ggt tcc      816
Thr Val Thr Ser Ala Asn Ser Gly Leu Asp Met Thr Met Pro Gly Ser
    240                 245                 250 gat tac tcc gat acc ccc tcc tcc gtc ctt tgg ggt cag aac ctg gcc      864
Asp Tyr Ser Asp Thr Pro Ser Ser Val Leu Trp Gly Gln Asn Leu Ala
255                 260                 265                 270 aac gcc atc tcc tcc ggc cag gtt gcc cag tcg cgt ctc gac gat atg      912
Asn Ala Ile Ser Ser Gly Gln Val Ala Gln Ser Arg Leu Asp Asp Met
                275                 280                 285 gtg act cgc att ttg gct gct tgg tac ttg gtt ggt cag gat cag ggc      960
Val Thr Arg Ile Leu Ala Ala Trp Tyr Leu Val Gly Gln Asp Gln Gly
            290                 295                 300 ttc cct gcg gtg gcc ttc aac tct tgg acc ggt ggt cag gcc tcc gtt     1008
Phe Pro Ala Val Ala Phe Asn Ser Trp Thr Gly Gly Gln Ala Ser Val
        305                 310                 315 aac gtc acc tcc aac cac aac cag gtt gcc cgt gcc gtc gct cgc gat     1056
Asn Val Thr Ser Asn His Asn Gln Val Ala Arg Ala Val Ala Arg Asp
    320                 325                 330 tct atc gtt ttg ctt aag aac acc aac agc acc ctt ccc ttg aac aag     1104
Ser Ile Val Leu Leu Lys Asn Thr Asn Ser Thr Leu Pro Leu Asn Lys
335                 340                 345                 350 ccc tcg agc att gct att att ggc act gac gcc cag acc aac cct tcc     1152
Pro Ser Ser Ile Ala Ile Ile Gly Thr Asp Ala Gln Thr Asn Pro Ser
```

-continued

|  |  |  | 355 |  |  |  | 360 |  |  |  | 365 |  |  |  |
|---|---|---|---|---|---|---|---|---|---|---|---|---|---|---|
| ggt | ccc | aac | gct | tgc | act | gat | cgt | ggt | tgc | gat | act | gga | act | ttg gct | 1200 |
| Gly | Pro | Asn | Ala | Cys | Thr | Asp | Arg | Gly | Cys | Asp | Thr | Gly | Thr | Leu Ala |  |
|  |  | 370 |  |  |  | 375 |  |  |  | 380 |  |  |  |  |  |

```
ggt ccc aac gct tgc act gat cgt ggt tgc gat act gga act ttg gct    1200
Gly Pro Asn Ala Cys Thr Asp Arg Gly Cys Asp Thr Gly Thr Leu Ala
        370                 375                 380 atg ggt tgg ggt tcc gga act tgc cag ttc ccc tac ctc acc gat cct    1248
Met Gly Trp Gly Ser Gly Thr Cys Gln Phe Pro Tyr Leu Thr Asp Pro
            385                 390                 395 ctc acc gct att aag act cgc gct gcc agc gac ggt act acc atc acc    1296
Leu Thr Ala Ile Lys Thr Arg Ala Ala Ser Asp Gly Thr Thr Ile Thr
    400                 405                 410 acc agc att tcc gac aac ggc tcc gcg gga gcc tcc gtt gct cag agc    1344
Thr Ser Ile Ser Asp Asn Gly Ser Ala Gly Ala Ser Val Ala Gln Ser
415                 420                 425                 430 gcc gag tac gcc atc gtt ttc atc aac tcc gac tct ggc gaa ggt tac    1392
Ala Glu Tyr Ala Ile Val Phe Ile Asn Ser Asp Ser Gly Glu Gly Tyr
                435                 440                 445 atc acc gtc gaa ggc gtc gct ggt gac cgc aac aac ctc gac ccc tgg    1440
Ile Thr Val Glu Gly Val Ala Gly Asp Arg Asn Asn Leu Asp Pro Trp
            450                 455                 460 cac tcc ggc aac gcc ctc gtg cag tcc gtc gcc gcc gtc aac aag aag    1488
His Ser Gly Asn Ala Leu Val Gln Ser Val Ala Ala Val Asn Lys Lys
        465                 470                 475 acc att gtc gtc att cac agc gtc ggt ccc gtc att ctt gaa acc atc    1536
Thr Ile Val Val Ile His Ser Val Gly Pro Val Ile Leu Glu Thr Ile
    480                 485                 490 ttg gcg cag cct aac gtt gtg gcc gtc gtc tgg gct ggc atc ccc gga    1584
Leu Ala Gln Pro Asn Val Val Ala Val Val Trp Ala Gly Ile Pro Gly
495                 500                 505                 510 cag gag agc ggc tcc gcc ctc acc gat atc ctc tac ggt tcc acc gct    1632
Gln Glu Ser Gly Ser Ala Leu Thr Asp Ile Leu Tyr Gly Ser Thr Ala
                515                 520                 525 ccc tcc gga aag ctc acc tac acc att gcc aag cag gct tcc gat tac    1680
Pro Ser Gly Lys Leu Thr Tyr Thr Ile Ala Lys Gln Ala Ser Asp Tyr
            530                 535                 540 ggc act gcc gtc gtc tcc ggt agc gac aac tac ccc gag gga ctt ttc    1728
Gly Thr Ala Val Val Ser Gly Ser Asp Asn Tyr Pro Glu Gly Leu Phe
        545                 550                 555 att gat tac cgc cac ttc gac aag agc aac att gaa cct cgc tac gaa    1776
Ile Asp Tyr Arg His Phe Asp Lys Ser Asn Ile Glu Pro Arg Tyr Glu
    560                 565                 570 ttc ggc tac gga ctg tcc tac acc acc ttc ggt tac acc aac ttg gcc    1824
Phe Gly Tyr Gly Leu Ser Tyr Thr Thr Phe Gly Tyr Thr Asn Leu Ala
575                 580                 585                 590 att gat att acc gtt tcg acc ggc ccc act act ggt cag atc gtt cct    1872
Ile Asp Ile Thr Val Ser Thr Gly Pro Thr Thr Gly Gln Ile Val Pro
                595                 600                 605 ggt gga cct tct gat ctt ttc gag tct gtt gga acc gtt acc gtc cag    1920
Gly Gly Pro Ser Asp Leu Phe Glu Ser Val Gly Thr Val Thr Val Gln
            610                 615                 620 gtc gcc aac acc ggc agc gtt gcc ggc tcc gaa gtt gcc cag ctc tac    1968
Val Ala Asn Thr Gly Ser Val Ala Gly Ser Glu Val Ala Gln Leu Tyr
        625                 630                 635 att ggt ctg ccc tcg tcc gcc ccc tcc tcc ccc ccc aag cag ttg cgt    2016
Ile Gly Leu Pro Ser Ser Ala Pro Ser Ser Pro Pro Lys Gln Leu Arg
    640                 645                 650 ggt ttc gat aag ctt tct ctc gct gct ggc gct agc ggt acc gcc acc    2064
Gly Phe Asp Lys Leu Ser Leu Ala Ala Gly Ala Ser Gly Thr Ala Thr
655                 660                 665                 670 ttc gat ttg acc cgc cgc gat ttg tcc tac tgg gat gtc tcc aag cag    2112
```

```
Phe Asp Leu Thr Arg Arg Asp Leu Ser Tyr Trp Asp Val Ser Lys Gln
                675             680             685 aag tgg gtg gtt ccc agc gga gcc ttc acc gtc tac gtt ggt gcc tcg    2160
Lys Trp Val Val Pro Ser Gly Ala Phe Thr Val Tyr Val Gly Ala Ser
        690             695             700 tcc cgc gat att cgc ttg cag ggt acc ttc acc ccc gga ggt agc tcg    2208
Ser Arg Asp Ile Arg Leu Gln Gly Thr Phe Thr Pro Gly Gly Ser Ser
        705             710             715 acc act tcg act atc act tcc tct aag act tct act act atc agc act    2256
Thr Thr Ser Thr Ile Thr Ser Ser Lys Thr Ser Thr Thr Ile Ser Thr
        720             725             730 tct gtt acc acc tcc agc tcc acc acc gct aag acc acc acc act agc    2304
Ser Val Thr Thr Ser Ser Ser Thr Thr Ala Lys Thr Thr Thr Thr Ser
735             740             745             750 tcg acc acc tcc tct gcc ggt ccc acc cag acc ccc tac gga cag tgc    2352
Ser Thr Thr Ser Ser Ala Gly Pro Thr Gln Thr Pro Tyr Gly Gln Cys
                755             760             765 ggt gga cag ggt tgg acc ggc cct acc gtg tgc tcc tct ggc tgg act    2400
Gly Gly Gln Gly Trp Thr Gly Pro Thr Val Cys Ser Ser Gly Trp Thr
        770             775             780 tgc aag gtc acc aac cag tgg tac tct cag tgc ctc cag tag            2442
Cys Lys Val Thr Asn Gln Trp Tyr Ser Gln Cys Leu Gln
        785             790             795

<210> SEQ ID NO 5
<211> LENGTH: 813
<212> TYPE: PRT
<213> ORGANISM: Acremonium cellulolyticus

<400> SEQUENCE: 5

Met Tyr Ser Ala Phe Leu Leu Leu Ala Ser Ala Thr Pro Ile Val
            -15             -10             -5

Ser Ala Gln Ser Ala Ser Trp Ser Ala Ala Tyr Ser Lys Ala Thr Ala
    -1  1           5                   10

Ala Leu Ser Lys Leu Ser Gln Asn Asp Lys Ile Gly Met Val Thr Gly
15              20              25              30

Val Gly Trp Gly Lys Gly Pro Cys Val Gly Asn Thr Ala Ala Pro Ser
                35              40              45

Gly Ile Ser Phe Pro Ser Leu Cys Ile Gln Asp Ser Pro Leu Gly Val
            50              55              60

Arg Tyr Ala Asn Pro Val Thr Ala Phe Pro Ala Gly Thr Asn Ala Gly
65              70              75

Met Thr Trp Asp Arg Thr Leu Met Asn Gln Arg Gly Ala Ala Leu Gly
        80              85              90

Ala Glu Ser Lys Gly Leu Gly Val His Val Gln Leu Gly Pro Val Ala
95              100             105             110

Gly Pro Leu Gly Lys Ile Ala Gln Gly Gly Arg Gly Trp Glu Gly Phe
                115             120             125

Gly Thr Asp Pro Tyr Leu Ser Gly Val Ala Met Ile Glu Thr Ile Ser
            130             135             140

Gly Met Gln Ser Ser Gly Thr Gln Ala Cys Ala Lys His Tyr Ile Gly
        145             150             155

Asn Glu Gln Glu Leu Asn Arg Glu Ser Met Ser Ser Asn Ile Asp Asp
        160             165             170

Arg Thr Leu His Glu Leu Tyr Leu Trp Pro Phe Ala Asp Ala Val Arg
175             180             185             190

Ala Asn Val Ala Ser Val Met Cys Ser Tyr Asn Gln Ile Asn Gly Thr
```

```
              195                 200                 205
Phe Ser Cys Glu Asn Glu Ser Met Thr Gly Ile Leu Lys Thr Glu
            210                 215                 220

Leu Gly Phe Pro Gly Tyr Ile Met Ser Asp Trp Asp Ala Gln His Thr
            225                 230                 235

Thr Val Thr Ser Ala Asn Ser Gly Leu Asp Met Thr Met Pro Gly Ser
240                 245                 250

Asp Tyr Ser Asp Thr Pro Ser Ser Val Leu Trp Gly Gln Asn Leu Ala
255                 260                 265                 270

Asn Ala Ile Ser Ser Gly Gln Val Ala Gln Ser Arg Leu Asp Asp Met
                275                 280                 285

Val Thr Arg Ile Leu Ala Ala Trp Tyr Leu Val Gly Gln Asp Gln Gly
            290                 295                 300

Phe Pro Ala Val Ala Phe Asn Ser Trp Thr Gly Gly Gln Ala Ser Val
                305                 310                 315

Asn Val Thr Ser Asn His Asn Gln Val Ala Arg Ala Val Ala Arg Asp
            320                 325                 330

Ser Ile Val Leu Leu Lys Asn Thr Asn Ser Thr Leu Pro Leu Asn Lys
335                 340                 345                 350

Pro Ser Ser Ile Ala Ile Ile Gly Thr Asp Ala Gln Thr Asn Pro Ser
                    355                 360                 365

Gly Pro Asn Ala Cys Thr Asp Arg Gly Cys Asp Thr Gly Thr Leu Ala
                370                 375                 380

Met Gly Trp Gly Ser Gly Thr Cys Gln Phe Pro Tyr Leu Thr Asp Pro
            385                 390                 395

Leu Thr Ala Ile Lys Thr Arg Ala Ala Ser Asp Gly Thr Thr Ile Thr
            400                 405                 410

Thr Ser Ile Ser Asp Asn Gly Ser Ala Gly Ala Ser Val Ala Gln Ser
415                 420                 425                 430

Ala Glu Tyr Ala Ile Val Phe Ile Asn Ser Asp Ser Gly Glu Gly Tyr
                    435                 440                 445

Ile Thr Val Glu Gly Val Ala Gly Asp Arg Asn Asn Leu Asp Pro Trp
            450                 455                 460

His Ser Gly Asn Ala Leu Val Gln Ser Val Ala Ala Val Asn Lys Lys
            465                 470                 475

Thr Ile Val Val Ile His Ser Val Gly Pro Val Ile Leu Glu Thr Ile
            480                 485                 490

Leu Ala Gln Pro Asn Val Val Ala Val Val Trp Ala Gly Ile Pro Gly
495                 500                 505                 510

Gln Glu Ser Gly Ser Ala Leu Thr Asp Ile Leu Tyr Gly Ser Thr Ala
                515                 520                 525

Pro Ser Gly Lys Leu Thr Tyr Thr Ile Ala Lys Gln Ala Ser Asp Tyr
                530                 535                 540

Gly Thr Ala Val Val Ser Gly Ser Asp Asn Tyr Pro Glu Gly Leu Phe
            545                 550                 555

Ile Asp Tyr Arg His Phe Asp Lys Ser Asn Ile Glu Pro Arg Tyr Glu
            560                 565                 570

Phe Gly Tyr Gly Leu Ser Tyr Thr Thr Phe Gly Tyr Thr Asn Leu Ala
575                 580                 585                 590

Ile Asp Ile Thr Val Ser Thr Gly Pro Thr Thr Gly Gln Ile Val Pro
                    595                 600                 605

Gly Gly Pro Ser Asp Leu Phe Glu Ser Val Gly Thr Val Thr Val Gln
                610                 615                 620
```

```
Val Ala Asn Thr Gly Ser Val Ala Gly Ser Glu Val Ala Gln Leu Tyr
            625                 630                 635

Ile Gly Leu Pro Ser Ser Ala Pro Ser Pro Pro Lys Gln Leu Arg
        640                 645                 650

Gly Phe Asp Lys Leu Ser Leu Ala Ala Gly Ala Ser Gly Thr Ala Thr
655                 660                 665                 670

Phe Asp Leu Thr Arg Arg Asp Leu Ser Tyr Trp Asp Val Ser Lys Gln
                675                 680                 685

Lys Trp Val Val Pro Ser Gly Ala Phe Thr Val Tyr Val Gly Ala Ser
            690                 695                 700

Ser Arg Asp Ile Arg Leu Gln Gly Thr Phe Thr Pro Gly Gly Ser Ser
            705                 710                 715

Thr Thr Ser Thr Ile Thr Ser Ser Lys Thr Ser Thr Thr Ile Ser Thr
        720                 725                 730

Ser Val Thr Thr Ser Ser Ser Thr Thr Ala Lys Thr Thr Thr Thr Ser
735                 740                 745                 750

Ser Thr Thr Ser Ser Ala Gly Pro Thr Gln Thr Pro Tyr Gly Gln Cys
                755                 760                 765

Gly Gly Gln Gly Trp Thr Gly Pro Thr Val Cys Ser Ser Gly Trp Thr
            770                 775                 780

Cys Lys Val Thr Asn Gln Trp Tyr Ser Gln Cys Leu Gln
        785                 790                 795

<210> SEQ ID NO 6
<211> LENGTH: 13
<212> TYPE: PRT
<213> ORGANISM: Acremonium cellulolyticus

<400> SEQUENCE: 6

Gly Pro Phe Val Gly Asn Thr Ala Ala Pro Ser Gly Ile
1               5                   10

<210> SEQ ID NO 7
<211> LENGTH: 12
<212> TYPE: PRT
<213> ORGANISM: Acremonium cellulolyticus

<400> SEQUENCE: 7

Thr Glu Leu Gly Phe Pro Gly Tyr Ile Met Ser Asp
1               5                   10

<210> SEQ ID NO 8
<211> LENGTH: 26
<212> TYPE: DNA
<213> ORGANISM: Artificial Sequence
<220> FEATURE:
<223> OTHER INFORMATION: primer:BGLB-F
<220> FEATURE:
<221> NAME/KEY: misc_feature
<222> LOCATION: (3)..(3)
<223> OTHER INFORMATION: "n" stands for any base
<220> FEATURE:
<221> NAME/KEY: misc_feature
<222> LOCATION: (9)..(9)
<223> OTHER INFORMATION: "n" represents an inosine
<220> FEATURE:
<221> NAME/KEY: misc_feature
<222> LOCATION: (12)..(12)
<223> OTHER INFORMATION: "n" represents an inosine
<220> FEATURE:
<221> NAME/KEY: misc_feature
<222> LOCATION: (18)..(18)
<223> OTHER INFORMATION: "n" stands for any base
```

```
<220> FEATURE:
<221> NAME/KEY: misc_feature
<222> LOCATION: (21)..(21)
<223> OTHER INFORMATION: "n" represents an inosine
<220> FEATURE:
<221> NAME/KEY: misc_feature
<222> LOCATION: (24)..(24)
<223> OTHER INFORMATION: "n" represents an inosine

<400> SEQUENCE: 8
ccnttygtng gnaayacngc ngcncc                                      26

<210> SEQ ID NO 9
<211> LENGTH: 21
<212> TYPE: DNA
<213> ORGANISM: Artificial Sequence
<220> FEATURE:
<223> OTHER INFORMATION: primer:BGLB-R
<220> FEATURE:
<221> NAME/KEY: misc_feature
<222> LOCATION: (10)..(10)
<223> OTHER INFORMATION: "n" stands for any base
<220> FEATURE:
<221> NAME/KEY: misc_feature
<222> LOCATION: (13)..(13)
<223> OTHER INFORMATION: "n" represents an inosine
<220> FEATURE:
<221> NAME/KEY: misc_feature
<222> LOCATION: (19)..(19)
<223> OTHER INFORMATION: "n" represents an inosine

<400> SEQUENCE: 9
catdatrtan ccnggraanc c                                           21

<210> SEQ ID NO 10
<211> LENGTH: 20
<212> TYPE: DNA
<213> ORGANISM: Artificial Sequence
<220> FEATURE:
<223> OTHER INFORMATION: praimer:BGLB-inv-F

<400> SEQUENCE: 10
taggcgttcg ttatgcgaac                                             20

<210> SEQ ID NO 11
<211> LENGTH: 20
<212> TYPE: DNA
<213> ORGANISM: Artificial Sequence
<220> FEATURE:
<223> OTHER INFORMATION: primer:BGLB-inv-R

<400> SEQUENCE: 11
aaacgagatt ccagatggcg                                             20

<210> SEQ ID NO 12
<211> LENGTH: 20
<212> TYPE: DNA
<213> ORGANISM: Artificial Sequence
<220> FEATURE:
<223> OTHER INFORMATION: primer:pBGLB-F

<400> SEQUENCE: 12
ctggacctat attccccgat                                             20

<210> SEQ ID NO 13
<211> LENGTH: 20
<212> TYPE: DNA
<213> ORGANISM: Artificial Sequence
<220> FEATURE:
```

```
<223> OTHER INFORMATION: primer:pBGLB-R

<400> SEQUENCE: 13
tggtttgtcc atactgcgtc                                                    20

<210> SEQ ID NO 14
<211> LENGTH: 25
<212> TYPE: DNA
<213> ORGANISM: Artificial Sequence
<220> FEATURE:
<223> OTHER INFORMATION: primer:BGLB-N

<400> SEQUENCE: 14
atgtattccg catttctttt gctgc                                              25

<210> SEQ ID NO 15
<211> LENGTH: 25
<212> TYPE: DNA
<213> ORGANISM: Artificial Sequence
<220> FEATURE:
<223> OTHER INFORMATION: primer:BGLB-C

<400> SEQUENCE: 15
ctattgtagg cattgagaat accat                                              25
```